United States Patent
Russell et al.

(12)

(10) Patent No.: US 6,750,206 B2
(45) Date of Patent: Jun. 15, 2004

(54) COMPOSITIONS AND METHODS FOR ELIMINATION OF UNWANTED CELLS

(75) Inventors: Stephen James Russell, Cambridge (GB); Frances Joanne Morling, Cambridge (GB); Adele Kay Fielding, Cambridge (GB); Francois-Loic Cosset, Lyons (FR); Roberto Cattaneo, Zurich (CH)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 09/070,630

(22) Filed: Apr. 30, 1998

(65) Prior Publication Data

US 2003/0095947 A1 May 22, 2003

Related U.S. Application Data

(63) Continuation of application No. PCT/GB98/00710, filed on Mar. 10, 1998.
(60) Provisional application No. 60/045,164, filed on Apr. 30, 1997.

(51) Int. Cl.$^7$ .................. A01N 43/04; A01N 63/00; C12N 5/00; C12N 15/00; C12N 15/63
(52) U.S. Cl. .................. 514/44; 424/93.2; 424/93.21; 435/320.1; 435/325; 435/440; 435/455
(58) Field of Search .................. 536/23.1, 23.5; 530/350; 435/320.1, 440, 455, 456, 325; 514/44; 424/93.2, 93.21

(56) References Cited

U.S. PATENT DOCUMENTS 5,753,499 A * 5/1998 Meruelo et al. .......... 435/320.1
5,847,096 A * 12/1998 Schubert et al. ........... 536/23.4
5,869,036 A * 2/1999 Belshe et al. .............. 424/93.2

FOREIGN PATENT DOCUMENTS

WO   WO 96/30030   3/1996

OTHER PUBLICATIONS

Messling et al., 2001, Journal of Virology, vol. 75, No. 14, p. 6418–6427.*
Wild et al., 1991, Journal of General Virology, vol. 72, No. 2, p. 439–442.*
Richardson et. al.; The Nucleotide Sequence of the mRNA Encoding the Fusion Protein of . . . from Several Different Paramyxovirus, 1986, Virology 155: 508–523.*
Rudinger et al., Characteristics of the amino acids as components of a peptied hormone sequence, 1976, Peptide Hormones, pp. 1–7.*
Kaye et al., A singel amino acid substitution results in a retinoblastoma protein defective in phosphorylation and oncoprotein binding, Sep. 1990, Proc.Natl.Acad. Sci., vol. 87, pp. 6922–6926.*
Heminway et al., Analysis of Respiratory Syncytial Virus F, G, and SH Protein in Cell Fusion, 1994, Virology, vol. 200 pp. 801–805.*
Ward et al., Mutants of the Paramyxovirus SV5 Fusion Protein Regulated and Extensive Syncytium Formation, 1995, Virology, vol. 209, pp. 242–249.*
Andeweg et al., Both the V2 and V3 Regions of the Human Immunodeficiency Virus Type 1 Surface Glycoprotein . . . , Jun. 1993, Journal Virology, vol. 67, No. 6, pp. 3232–3239.*
Otteken et al., Mapping of the Human Immunodeficiency Virus Type 2 Envelope Glycoprotein CD4 Binding Region and Fusion Domain with Truncatefd Protein Expressed by Recombinant Vaccinia Viruses, 1993, Virology, vol. 194, pp. 37–43.*
Verma et al. Gene therapy–promises, problems and prospects. Nature, vol. 389, pp. 239–242, Sep. 18, 1997.*
Eck et al. Gene–Based Therapy. Goodman & Gilman's The Pharmacological Basis of Therapeutics, 9th edition, Chapter 5, pp. 77–101, 1996.*
Asada, Teruo (1974) Treatment of Human Cancer with Mumps Virus. *Cancer,* 34:1907–1928.
Russell, Stephen J. (1994) Replicating Vectors for Cancer Therapy: A Question of Strategy. *Cancer Biology,* 5:437–443.
Russell, Stephen J. (1994) Replicating Vectors for Gene Therapy of Cancer: Risks, Limitations, and Prospects. *European Journal of Cancer,* vol. 30A, 8:1165–1171.

* cited by examiner

*Primary Examiner*—Shin-Lin Chen
(74) *Attorney, Agent, or Firm*—Fish & Richardson P.C., P.A.

(57) ABSTRACT

Disclosed are compositions comprising a recombinant nucleic acid vector including a nucleotide sequence encoding a syncytium-inducing polypeptide expressible on a eukaryotic cell surface, and a host cell containing the recombinant vector and expressing the syncytium inducing polypeptide on its cell surface, the vectors and resultant host cells expressing the syncytium inducing polypeptide being useful for selective elimination of unwanted cells.

4 Claims, 7 Drawing Sheets

```
1/1
atg gta ttg ctg cct ggg tcc atg ctt ctc aac ctg cac cac ctt cgg cac cag             cct ggg agc tgg aaa aga ctg atc
 M   V   L   L   P   G   S   M   L   L   N   L   H   H   L   R   H   Q              P   G   S   W   K   R   L   I
91/31                                                                        61/21
atc ctc tta agc tgc gta ttc ggc ggc ggc agt acg ggg caa ctg ctg cac ccc      atg agt cag ccc atg acc ctc act gta ctg
 I   L   L   S   C   V   F   G   G   G   S   T   G   Q   L   L   H   P       M   S   Q   P   M   T   L   T   V   L
181/61                                                                       151/51
tcc caa act gga gac gtt gtc tgg gat aca aag gca ccc cag tgg act tgg          ctt aaa cct gat gta tgt gcc ttg
 S   Q   T   G   D   V   V   W   D   T   K   A   P   Q   W   T   W           L   K   P   D   V   C   A   L
271/91                                                                       241/81
gcg gct agt ctt gag tcc tgg gat atc ccg gga acc gat gtc tcg tct aaa cga gtc  ccc aca ctt ccg gac tca gac tat act gcc gct
 A   A   S   L   E   S   W   D   I   P   G   T   D   V   S   S   K   R   V   P   T   L   P   D   S   D   Y   T   A   A
361/121                                                                      331/111
tat aag caa atc acc tgg gga gcc ata ggg tgc agc tac cct cgg gct agg act aga atg  aga cct acc ttc tgt ccc cgg
 Y   K   Q   I   T   W   G   A   I   G   C   S   Y   P   R   A   R   T   R   M    R   P   T   F   C   P   R
451/151                                                                      421/141
gat ggc cgg tgt tca gaa ctt aaa tcc tca aaa gct aga agg tgc ggg cta gaa tcc cta tac tgt aaa  gca agc tct gag tgt ggg acc ggt
 D   G   R   C   S   E   L   K   S   S   K   A   R   R   C   G   L   E   S   L   Y   C   K    A   S   S   E   W   T   G
541/181                                                                      511/171
tat tgg cta tct aaa tcc ttt aaa ata gat cta aaa ata act agt tgg cta ata act gta aaa tgg caa caa aat agc gaa   caa aaa ttt caa cag cac cag
 Y   W   L   S   K   S   F   K   I   D   L   K   I   T   S   W   L   I   T   V   K   W   Q   Q   N   S   E    Q   K   F   Q   Q   H   Q
633/211                                                                      601/201
acc ggc tgg tgt aac ccc ctt aaa ata gat ttc aca ata gga gga aaa tta tcc aag gac      gat tgt gag ggg gga tta aga
 T   G   W   C   N   P   L   K   I   D   F   T   I   G   G   K   L   S   K   D       D   C   E   G   G   L   R
721/241                                                                      691/231
ttc tat gtg tct gga cat gga cct cca gga gta cag ttc acc att cgc tta aaa ata   tgg ata acc aag acc aac atg cct gac ctc gtc
 F   Y   V   S   G   H   G   P   P   G   V   Q   F   T   I   R   L   K   I    W   I   T   K   T   N   M   P   D   L   V
811/271                                                                      781/261
ctt gtg gaa gga cct aga acg tcc ctc gct cca cct ctt gcg aga aaa ata cgg     cca gct gaa gcg agg cca ccg cct ctc gac tct
 L   V   E   G   P   R   T   S   L   A   P   P   L   A   R   K   I   R      P   A   E   A   R   P   P   P   L   D   S
901/301                                                                      871/291
aac tcc aca gcc ctg gcg act agt gca caa acc ttc gtc aat gct acc aac cca    gaa gcg gaa gcg cca cct ccg cct ccc acc agg ggc
 N   S   T   A   L   A   T   S   A   Q   T   F   V   N   A   T   N   P     E   A   E   A   P   P   P   P   T   R   G
991/331                                                                      961/321
aga ctt ttt gat ctt gtg cag ggg gcc ttc cta acc ttc tta gag gag gtc gcc    cta aac act gag tct tgc tgg ttg gcc atg
 R   L   F   D   L   V   Q   G   A   F   L   T   F   L   E   E   V   A     L   N   T   E   S   C   W   L   A   M
1081/361                                                                     1051/351
ggc ccc cct tat tat gaa gca ata gca gcc tca tca gga gag gtc gcc tac tcc acc gac ctt    gac cgg tgc tgc cgc tgg gga acc gga aag
 G   P   P   Y   Y   E   A   I   A   A   S   S   G   E   V   A   Y   S   T   D   L     D   R   C   C   R   W   G   T   G   K
                                                                             1141/381
```

COMPOSITIONS AND METHODS FOR ELIMINATION OF UNWANTED CELLS

RELATED APPLICATIONS

This application is a continuation of and claims benefit to PCT/GB98/00710, filed Mar. 10, 1998, which claims benefit of U.S. Ser. No. 60/045,164, filed Apr. 30, 1997 and UK 9705007.4, filed Mar. 11, 1997.

FIELD OF THE INVENTION

This invention relates to genes encoding fusogenic viral membrane glycoproteins and cells expressing such genes.

BACKGROUND OF THE INVENTION

Prior art methods of treating cell proliferative disorders such as cancer have involved introduction into a patient of genes or vehicles containing genes encoding, for example, proteins that enhance the immunogenicity of tumor cells. These include pro-inflammatory cytokines, T cell co-stimulators and foreign MHC proteins which produce a local bystander effect due to local inflammatory response. The local inflammatory response is said to create a cytokine-rich environment which favors the generation of a systemic bystander effect by recruitment and activation of tumor-specific T cells.

Alternatively, it has been suggested to deliver to a tumor genes encoding enzymes that render tumor cells susceptible to a "pro-drug". For thymidine kinase gene transfer, there is some evidence for a local bystander effect due to transfer of ganciclovir triphosphate (the activated drug) through tight junctions to adjacent tumor cells. However, many tumors lack the requisite tight junctions and the observed local and systemic bystander effects are therefore presumed to arise because of a local inflammatory response to cells that are killed by the pro-drug with associated activation of tumor-reactive T cells.

Replicating viruses have been used extensively as oncolytic agents for experimental cancer therapy (Russell, 1994, Semin. Cancer Biol. 5, 437–443). For example, a tissue culture suspension of mumps virus was used to treat 90 patients with terminal malignancies by local application to the tumor surface, by intratumoral, oral, rectal or intravenous inoculation, or by inhalation (Asada, 1974, Cancer, 34, 1907–1928). Toxicity was minimal and in 37 of the 90 patients the tumor disappeared or decreased to less than half of its initial size. Minor responses were observed in a further 42 patients. Tumor destruction was maximal several days after virus administration and was often followed by long-term suppression of tumor growth, perhaps due to stimulation of antitumor immunity.

Other viruses that have been used for cancer therapy in human subjects or experimental mouse models include West Nile virus, herpes simplex virus, Russian Far East encephalitis, Newcastle disease virus, Venezuelan equine encephalomyelitis, rabies, vaccinia and varicella (Russell, 1994, Eur. J. Cancer, 30A, 1165–1171). The rationale for these studies has been that many viruses replicate and spread more rapidly in neoplastic tissues than in nontransformed tissues and might therefore be expected to cause more damage to the tumor than to the host.

It is an object of the invention to provide compositions and methods for selective elimination of unwanted cells.

Another object of the invention is to selectively eliminate target cells by achieving a bystander effect.

Another object of the invention is to selectively induce syncytium formation of target cells, thereby eliminating the target cells.

SUMMARY OF THE INVENTION

The invention encompasses compositions comprising pharmaceutical formulations comprising a recombinant nucleic acid vector comprising a nucleotide sequence encoding a syncytium-inducing polypeptide expressible on a eukaryotic cell surface in admixture with a pharmaceutically acceptable carrier.

The invention also encompasses compositions comprising pharmaceutical formulations comprising a eukaryotic host cell containing a recombinant nucleic acid vector comprising a nucleotide sequence encoding a syncytium-inducing polypeptide and expressing the polypeptide on its surface, in admixture with a pharmaceutically acceptable carrier.

Preferably, in a composition according to the invention the sequence encodes at least a fusogenic portion of a viral fusogenic membrane glycoprotein.

Preferably, the sequence encodes a non-naturally occurring polypeptide. "Non-naturally occurring polypeptide refers to a recombinant polypeptide; for example, a chimeric polypeptide.

Preferably, the sequence encodes a fusogenic membrane glycoprotein having an artificially introduced protease-cleavage site.

Preferably, the sequence encodes a fusogenic membrane glycoprotein having an altered binding specificity.

Preferably, the sequence encodes a fusogenic membrane glycoprotein having enhanced fusogenicity, for example, as results from truncation of the carboxy terminal portion of a fusogenic membrane glycoprotein.

The eukaryotic host cell may be a human cell, such as a host cell selected from the group consisting of neoplastic cells, migratory cells, T lymohocytes, B lymphocytes or other haemopoietic cells.

The invention also features a method of eliminating unwanted cells of a cell proliferative disease in a human patient, comprising administering to the patient a pharmaceutical formulation according to the invention in an amount sufficient to cause fusion of those cells which cause the cell proliferative disease.

The invention also encompasses kits comprising a pharmaceutical formulation described herein, and packaging means therefore.

Nucleic acid vectors and host cells of the invention are useful in gene therapy of diseases involving cell proliferative disorders, where it is desired that cells which proliferate undesirably or uncontrollably are selectively eliminated. Such diseases include but are not limited to malignant diseases. The vector encoding the syncytium-inducing polypeptide or a host cell expressing on its surface a syncytium-inducing polypeptide is administered to an affected individual so as to cause cell-cell fusion of unwanted cells.

Preferably, the syncytium-inducing polypeptide comprises at least a fusogenic portion of a viral fusogenic membrane glycoprotein (which may be abbreviated as FMG). In some embodiments, it is preferred that the syncytium-inducing polypeptide is capable of inducing syncytium formation at substantially neutral pH (i.e. pH 6–8). Many suitable FMGs will be known to those skilled in the art and several are provided hereinbelow.

Typically the vector will be adapted so as to express the syncytium-inducing polypeptide on the surface of a human cell, such that, when properly expressed, the polypeptide may cause the cell to fuse with other human cells which do not express the syncytium-inducing polypeptide.

It is preferred that, where the polypeptide comprises a viral FMG, the FMG is expressed in substantial isolation from other viral components and thus consists essentially of those viral components which are essential for fusogenic activity on target cells (e.g. where two viral glycoproteins are required for syncytium formation, such as the 'F' and 'H' glycoproteins of Paramyxoviridae both being required for syncytium-formation).

In addition, it will frequently be desirable to "engineer" the syncytium-inducing polypeptide to optimize its characteristics for therapeutic use, such that the vector directs the expression of a "non-naturally occurring" polypeptide.

Preferred modifications include truncation of the cytoplasmic domain of a glycoprotein so as to increase its fusiongenic activity; introduction of novel binding specificities or protease-dependencies into fusogenic viral membrane glycoproteins and thereby to target their fusogenic activities to specific cell types that express the targeted receptors or to specific microenvironments that are rich in the appropriate activating proteases.

The invention provides a method of treating a cell proliferative disease such as a malignant disease in a human patient, comprising administering to the patient a recombinant nucleic acid directing the expression of a syncytium inducing polypeptide in a human cell, such that cells ("index" cells) of the patient which take up the recombinant nucleic acid will fuse with the proliferating cells, e.g., cancerous cells ("target" cells) causing the disease.

In a particular embodiment, the nucleic acid is introduced in vitro into suitable human index cells (by any one of various known standard techniques, such as transfection, transduction or transformation), and the index cells are then introduced into the patient, where they can exert a syncytium-inducing effect on target cells.

The invention also provides for use of a recombinant nucleic acid vector in the gene therapy of a cell proliferative disorder such as a malignant disease, the vector comprising a sequence directing the expression on a eukaryotic cell surface of a syncytium-inducing polypeptide.

The invention also provides a recombinant nucleic acid vector for use in the preparation of a medicament to treat a cell proliferative disease such as a malignant disease in a human patient, the vector comprising a sequence directing the expression on a eukaryotic cell surface of a syncytium-inducing polypeptide.

The invention also provides a host cell comprising a recombinant nucleic acid vector in accordance with the invention defined above. The cell will typically be a eukaryotic cell (especially a human cell) and desirably will express on its surface a syncytium-inducing polypeptide.

As used herein, the term "syncytium inducing polypeptide" refers to a polypeptide or a portion thereof that induces cell-cell fusion resulting in formation of a syncytium.

The term "syncytium" refers to a cell-cell fusion which appears in a tissue biopsy or tissue culture sample as a large acellular area with multiple nucleii, i.e., a multinucleate region of cytoplasm.

"Enhanced induction of syncytium formation" refers to the biological activity of a syncytium inducing polypeptide in which the enhancement is an increase in the number of cells that are induced to form a syncytium above (at least 10–20%) the level of that observed without the syncytium inducing polypeptide or, if the syncytium inducing polypeptide is engineered to achieve the enhanced activity, then above the level of that observed using the non-engineered polypeptide. "Enhanced fusogenic activity" is also used herein to refer to enhanced syncytium inducing activity.

"Nonviable syncytium" refers to syncytium that do not survive for longer than 48–72 hours in tissue culture (i.e., in vitro), or a syncytium which is immunogenic (recognized by the immune system) in vivo and are nonviable in an immunocompetent host.

As used herein, the term "substantial isolation" of a viral polypeptide or gene encoding a viral polypeptide, with respect to other viral components, means that most of the other components of the virus (those not necessary for fusogenic activity of the virus polypeptide) are absent, and thus the DNA or viral polypeptide consists essentially of those viral components which are essential for fusogenic activity on target cells.

A "fusogenic effect" refers to the natural biological activity of a fusogenic polypeptide in inducing cell fusion via the presence of a virus encoding and expressing the fusogenic polypeptide. Virus-cell fusion and cell-cell fusion are distinct processes. "Fusogenic" refers to the biological activity of a viral membrane glycoprotein to promote virus-cell fusion when in its natural virus context. In contrast, "syncytium-induction" refers to the biological activity of a syncytium-inducing polypeptide, which may be a viral membrane glycoprotein substantially isolated from its natural virus context, to induce cell-cell fusion without the virus. To be useful according to the invention, a viral glycoprotein which has a fusogenic effect when carried in the virus must be capable of inducing syncytium formation when in substantial isolation from the virus.

A "fusogenic portion" refers to a portion of a fusogenic virus membrane polypeptide which possesses fusogenic activity and thus promotes virus-cell fusion.

"Altered receptor specificity" refers to a modification in a ligand such that the receptor recognized by the modified ligand is altered from a first receptor to a second receptor; that is, the unmodified ligand recognizes a first receptor and the modified ligand recognizes a second receptor.

"Novel protease-dependency" of a polypeptide according to the invention refers to the presence of a new protease sensitive site that is susceptible to cleavage where a site of proteolysis is artificially introduced into a given protein, and the protein containing the new sensitivity is dependent for becoming biologically active upon a protease that specifically cleaves the protein at the site of proteolysis; without cleavage by the protease at the new protease sensitive site, the protease-dependent polypeptide will not become biologically active.

A "vector system" refers to one vector or several vectors which together encode specified components.

The invention will now be further described by way of illustrative example and with reference to the accompanying drawing, FIG. 1, which is a schematic representation of a recombinant nucleic acid vector in accordance with the invention.

DRAWINGS

The invention will now be further described by way of illustrative example and with reference to the accompanying drawings in which:

FIGS. 1–3 are schematic representations of recombinant nucleic acid vectors; in FIG. 2 CMV is the CMV promoter; in FIGS. 1 and 3 LTR is the long terminal repeat; in FIG. 3 phleo$^r$ is the phleomycin resistance gene; in FIGS. 2 and 3 the IEGR (SEQ ID NO:14) linker sequence is the protease cleavage signal for FXa protease and * denotes stop codons (pCG-H EGF$^{R-}$ and pFBH EGF$^{R-}$ are SEQ ID NO:8; pCG-H XEGF$^{R-}$ and pFBH XEGF$^{R-}$ are SEQ ID NO:9; pCG-H IGF and pFBH IGF are SEQ ID NO:10; pCG-H XIGF and pFBH XIGF are SEQ ID NO:11);

Figure 6:
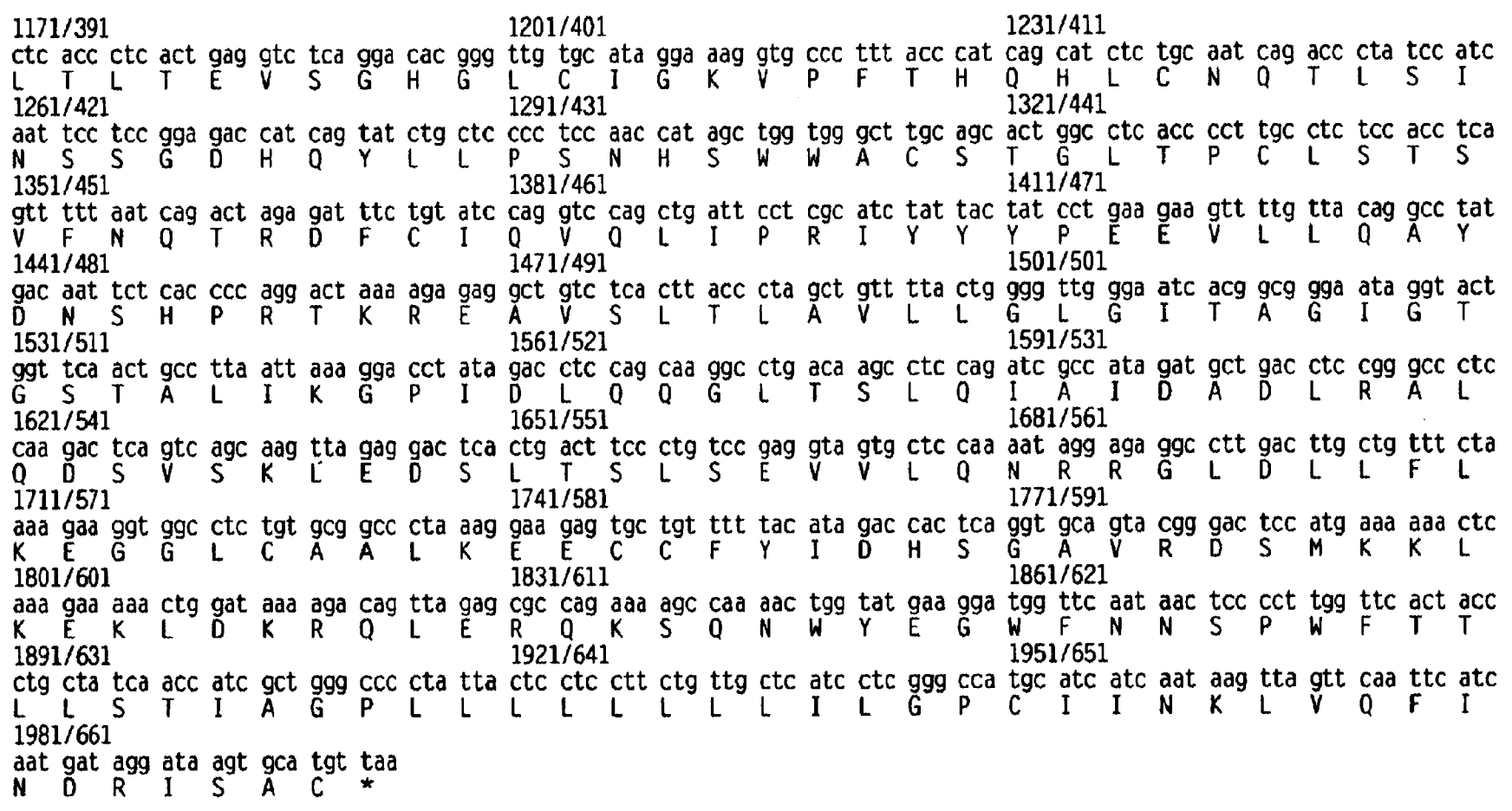
Figure 7:
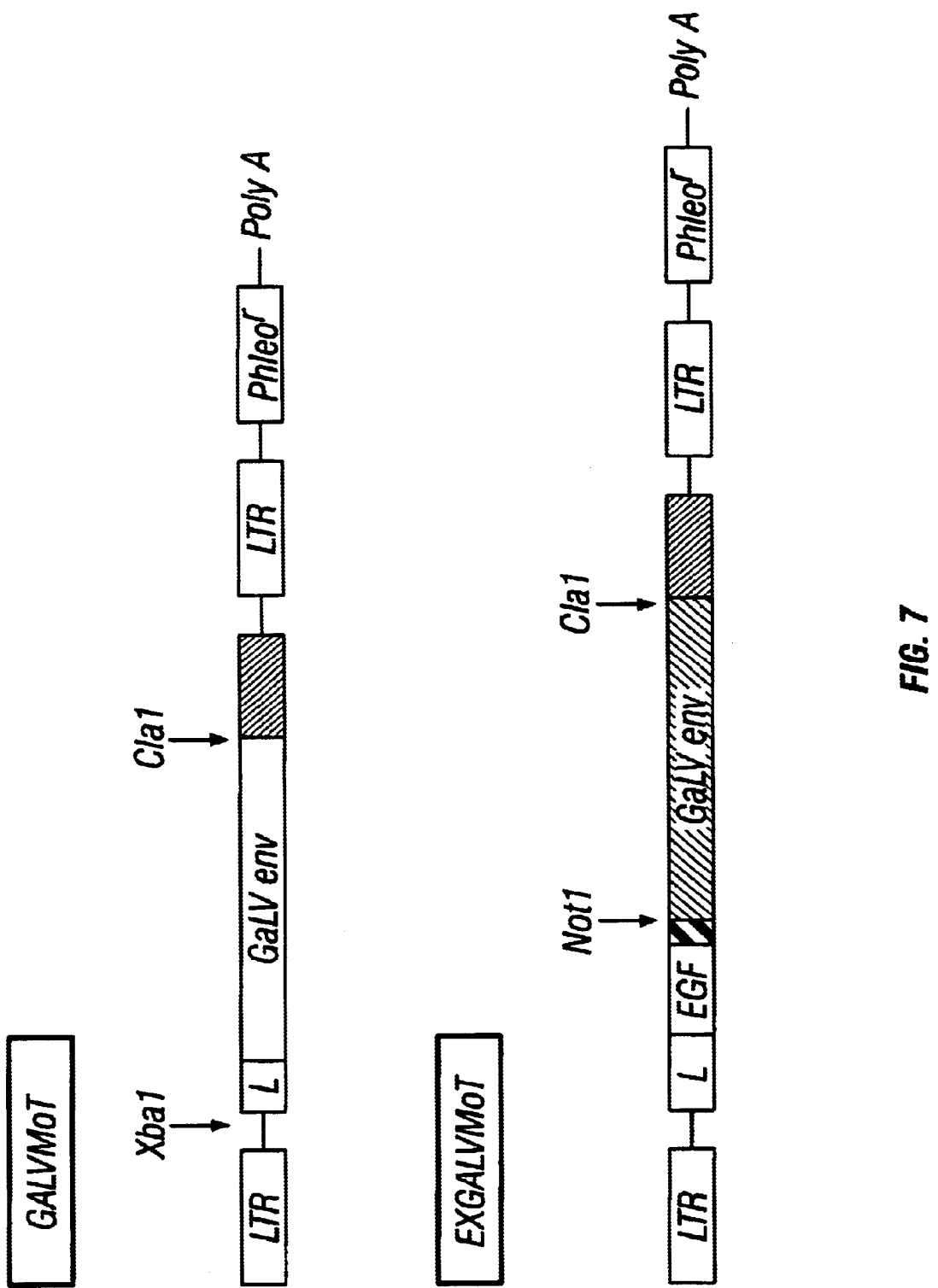

FIG. 6 shows the DNA and amino acid sequence of a truncated hyperfusogenic GaLV envelope protein (SEQ ID NOS:12 and 13, respectively); and FIG. 7 is a schematic representation of further recombinant nucleic acid vectors: in FIG. 7, the striped box is the FXa cleavage signal, the lightly shaded box is the mature (residues 43–653 only) GaLV envelope, and the heavily shaded box is residues 633–674 of the moloney MLV envelope, poly A is a polyadenylation signal, L is a leader sequence.

DESCRIPTION OF PREFERRED EMBODIMENTS

The invention finds its basis in the use of a syncytium-inducing polypeptide which, when expressed on the surface of a mammalian cell, is capable of causing that cell to fuse with neighboring cells that do not express the syncytium-inducing polypeptide, to form a nonviable syncytium and thereby to selectively eliminate unwanted cells. If desired, the syncytium-inducing polypeptide can be engineered for enhanced fusogenic activity, altered cell receptor specificity, or novel protease-dependency, as described herein.

The ideal syncytium-inducing polypeptide useful according to the invention is a protein that has the following properties:

1. Gives rise to a local bystander effect: i.e., the protein will lead to cell death of not only the transduced tumor cell, but also its nontransduced neighbors.
2. Gives rise to a systemic bystander effect. Usually, this means that the treatment has the effect of enhancing the immune response against tumor antigens on distant tumor cells.
3. Provides selectivity. It is important that the treatment does not cause undue damage to normal (noncancerous) host tissues, especially the vital organs. Selectivity can be an intrinsic property of the protein and/or arise from its mode of action. Alternatively, or additionally, selectivity can be achieved by vector targeting to ensure that a therapeutic gene encoding the protein is not delivered to nontarget cells, or by the use of gene regulatory elements (promoters/enhancers/silencers/locus control sequences) that do not give rise to gene expression in nontarget cells.

According to the invention, engineered/targeted fusogenic viral membrane glycoproteins satisfy all three criteria of local bystander effect, systemic bystander effect (by promoting a local inflammatory response which helps to amplify systemic immunity), and specificity. They have the capacity for generating a potent local bystander effect because they induce the fusion of gene-modified cells with surrounding nontransduced cells, resulting in the death of all the cells that have fused together. They can also be engineered to enhance their potential for triggering cell-cell fusion, and hence their therapeutic potency. Also, it is possible to engineer the specificity of the cell-cell fusion process by engineering the fusogenic proteins to ensure, for example, that circulating tumor cells that express the fusogenic proteins can fuse only with other tumor cells and do not therefore damage normal host tissues.

Characteristics of viral FMGs which may be susceptible to improvement by protein engineering include:

(1) pH at which fusion is mediated (as explained herein, many viral FMGs mediate fusion only at acid pH, whereas fusion at neutral pH may frequently be preferred);

(2) activation of the fusion function upon exposure to certain proteases (this can lead to localized activation at the surface of, or in the vicinity of, tumor cells, many of which secrete or express tumor-associated proteases, as explained hereinbelow in the section entitled "Protease targets"—accordingly the FMG can be targeted to tumor cells);

(3) modification of natural FMGs (e.g. amino acid substitutions, truncations or production of chimeric FMGS)—chimeric FMGs could comprise novel binding specificities to target the FMGs to particular cell surface markers, or combine other desirable characteristics from different proteins.

Syncytium-inducing polypeptides useful according to the invention may be selected from the following viral membrane glycoproteins.

Viral Membrane Glycoproteins Mediating Cell-Cell Fusion

The invention contemplates the use of a gene encoding a polypeptide for the selective induction of syncytium formation in target cells, and the selective elimination of these target cells via the induction of a syncytium. Syncytium-inducing polypeptides useful according to the invention include fusogenic membrane glycoproteins which include but are not limited to the following.

1) Membrane Glycoproteins of Enveloped Viruses.

Enveloped viruses have membrane spike glycoproteins for attachment to mammalian cell surfaces and for subsequent triggering of membrane fusion, allowing for viral entry into the cell. In some viruses attachment and fusion triggering are mediated by a single viral membrane glycoprotein, but in other viruses these functions are provided by two or more separate glycoproteins. Sometimes (e.g. Myxoviridae, Togaviridae, Rhabdoviridae) the fusion triggering mechanism is activated only after the virus has entered into the target cell by endocytosis, at acid pH (i.e., below about pH 6.0). Examples of such membrane glycoproteins in Rhabdoviruses are the those of type G in rabies (Genbank Acc. No. U11736), Mokola (Genbank Acc. No. U17064) and vesicular stomatitis (Genbank Acc. Nos. M21417 and J04326) viruses, and in Togaviruses, Other viruses (e.g. Paramyxoviridae, Retroviridae, Herpesviridae, Coronaviridae) can fuse directly with the target cell membrane at substantially neutral pH (about 6.0–8.0) and have an associated tendency to trigger membrane fusion between infected target cells and neighboring noninfected cells. The visible outcome of this latter tendency for triggering of cell-cell fusion is the formation of cell syncytia containing up to 100 nuclei (also known as polykaryocytes or multinucleated giant cells). Syncytium-formation results in the death of the cells which make up the syncytium. Viral membrane proteins of these latter groups of viruses are of particular interest in the present invention. In addition to those proteins from Paramyxoviruses, Retroviruses and Herpesviruses discussed below, examples of Coronavirus membrane glycoprotein genes include those encoding the murine hepatitis virus JHM surface projection protein (Genbank Acc. Nos. X04797, D00093 and M34437), porcine respiratory coronavirus spike- and membrane glycoproteins (Genbank Acc. No. Z24675) avian infectious bronchitis spike glycoprotein (Genbank Acc. No. X64737) and its precursor (Genbank Acc. No. X02342) and bovine enteric coronavirus spike protein (Genbank Acc. No. D00731).

2) Viral Membrane Glycoproteins of the Paramyxoviridae Viruses.

Viruses of the Family Paramyxoviridae have a strong tendency for syncytium induction which is dependent in most cases on the co-expression of two homo-oligomeric viral membrane glycoproteins, the fusion protein (F) and the viral attachment protein (H, HN or G). Co-expression of these paired membrane glycoproteins in cultured cell lines is required for syncytium induction although there are exceptions to this rule such as SV5 whose F protein alone is sufficient for syncytium induction. F proteins are synthesized initially as polyprotein precursors ($F_0$) which cannot trigger membrane fusion until they have undergone a cleavage activation. The activating protease cleaves the $F_0$ precursor into an extraviral $F_1$ domain and a membrane anchored $F_2$ domain which remain covalently associated through disulphide linkage. The activating protease is usually a serine protease and cleavage activation is usually mediated by an intracellular protease in the Golgi compartment during protein transport to the cell surface. Alternatively, where the cleavage signal is not recognized by a Golgi protease, the cleavage activation can be mediated after virus budding has occurred, by a secreted protease (e.g. trypsin or plasmin) in an extracellular location (Ward et al. Virology, 1995, 209, p 242–249; Paterson et al., J. Virol., 1989, 63, 1293–1301).

Examples of Paramyxovirus F genes include those of Measles virus (Genbank Acc. Nos. X05597 or D00090), canine distemper virus (Genbank Acc. No. M21849), Newcastle disease virus (Genbank Acc. No. M21881), human parainfluenza virus 3 (Genbank Acc. Nos. X05303 and D00125), simian virus 41 (Genbank Acc. Nos. X64275 and S46730), Sendai virus (Genbank Acc. No. D11446) and human respiratory syncytial virus (Genbank Acc. No. M11486, which also includes glycoprotein G). Also of interest of Measles virus hemagluttinin (Genbank Acc. No. M81895) and the hemagluttinin neuraminidase genes of simian virus 41 (Genbank Acc. Nos. X64275 or S46730), human parainfluenza virus type 3 (M17641) and Newcastle disease virus (Genbank Acc. No. J03911).

3) Membrane Glycoproteins of the Herpesvirus Family.

Certain members of the Herpesvirdae family are renowned for their potent syncytium-inducing activity. Indeed, Varicella-Zoster Virus has no natural cell-free state in tissue culture and spreads almost exclusively by inducing cell fusion, forming large syncytia which eventually encompass the entire monolayer. gH is a strongly fusogenic glycoprotein which is highly conserved among the herpesvirus; two such proteins are gH of human herpesvirus 1 (Genbank Acc. No. X03896) and simian varicella virus (Genbank Acc. No. U25806). Maturation and membrane expression of gH are dependent on coexpression of the virally encoded chaperone protein gL (Duus et al., Virology, 1995, 210, 429–440). Although gH is not the only fusogenic membrane glycoprotein encoded in the herpesvirus genome (gB has also been shown to induce syncytium formation), it is required for the expression of virus infectivity (Forrester et al., J. Virol., 1992, 66, 341–348). Representative genes encoding gB are found in human (Genbank Acc. No. M14923), bovine (Genbank Acc. No. Z15044) and cercopithecine (Genbank Acc. No. U12388) herpesviruses.

4) Membrane Glycoproteins of Retroviruses.

Retroviruses use a single homo-oligomeric membrane glycoprotein for attachment and fusion triggering. Each subunit in the oligomeric complex is synthesized as a polyprotein precursor which is proteolytically cleaved into membrane-anchored (TM) and extraviral (SU) components which remain associated through covalent or noncovalent interactions. Cleavage activation of the retroviral envelope precursor polypeptide is usually mediated by a Golgi protease during protein transport to the cell surface. There are inhibitory (R) peptides on the cytoplasmic tails of the TM subunits of the envelope glycoproteins of Friend murine leukemia virus (FMLV, EMBL accession number X02794) and Mason Pfizer monkey virus (MPMV; Genbank Acc. No. M12349) which are cleaved by the virally encoded protease after virus budding has occurred. Cleavage of the R peptide is required to activate fully the fusogenic potential of these envelope glycoproteins and mutants lacking the R peptide show greatly enhanced activity in cell fusion assays (Rein et al, J. Virol., 1994, 68, 1773–1781; Ragheb & Anderson, J. Virol., 1994, 68, 3220–3231; Brody et al, J. Virol. 1994, 68, 4620–4627).

5) MLV Membrane Glycoproteins with Altered Specificity.

Naturally occurring MLV strains can also differ greatly in their propensity for syncytium induction in specific cell types or tissues. One MLV variant shows a strong tendency to induce the formation of endothelial cell syncytia in cerebral blood vessels, leading to intracerebral hemorrhages and neurologic disease. The altered behavior of this MLV variant can be reproduced by introducing a single point mutation in the env gene of a non-neurovirulent strain of Friend MLV, resulting in a tryptophan-to-glycine substitution at amino acid position 120 in the variable region of the SU glycoprotein (Park et al, J. Virol., 1994, 68, 7516–7524).

6) HIV Membrane Glycoproteins.

HIV strains are also known to differ greatly in their ability to induce the formation of T cell syncytia and these differences are known to be determined in large part by variability between the envelope glycoproteins of different strains. Typical examples are provided by Genbank accessions L15085 (V1 and V2 regions) and U29433 (V3 region).

7) Acid-Triggered Fusogenic Glycoproteins Having an Altered pH Optimum.

The membrane glycoproteins of viruses that normally trigger fusion at acid pH do not usually promote syncytium formation. However, they can trigger cell-cell fusion under certain circumstances. For example, syncytia have been observed when cells expressing influenza haemagglutinin (Genbank Acc. No. U44483) or the G protein of Vesicular Stomatitis Virus (Genbank Acc. Nos. M21417 and J04326) are exposed to acid (Steinhauer et al, Proc. Natl. Acad. Sci. USA 1996, 93, 12873–12878) or when the fusogenic glycoproteins are expressed at a very high density (Yang et al, Hum. Gene Ther. 1995, 6, 1203–1213). In addition, acid-triggered fusogenic viral membrane glycoproteins can be mutated to shift their pH optimum for fusion triggering (Steinhauer et al, Proc. Natl. Acad. Sci. USA 1996, 93, 12873–12878).

8) Membrane Glycoproteins From Poxviruses.

The ability of poxviruses to cause cell fusion at neutral pH correlates strongly with a lack of HA production (Ichihashi & Dales, Virology, 1971, 46, 533–543). Wild type vaccinia virus, an HA-positive orthopoxvirus, does not cause cell fusion at neutral pH, but can be induced to do so by acid pH treatment of infected cells (Gong et al, Virology, 1990, 178, 81–91). In contrast, wild type rabbitpox virus, which lacks a HA gene, causes cell fusion at neutral pH. However, inactivation of the HA or SPI-3 (serpin) genes in HA-positive orthopoxviruses leads to the formation of syncytia by fusion of infected cells at neutral pH (Turner & Moyer, J. Virol. 1992, 66, 2076–2085). Current evidence indicates that the SPI-3 and HA gene products act through a common pathway to control the activity of the orthopoxvirus fusion-triggering viral glycoproteins, thereby preventing fusion of cells infected with wild type virus.

9) Membrane Glycoproteins of Other Replicating Viruses.

Replicating viruses are known to encode fusogenic viral membrane glycoproteins, which viruses include but are not limited to mumps virus (hemagglutinin neuraminidase, SwissProt P33480; glycoproteins F1 and F2, SwissProt P33481), West Nile virus (Genbank Acc. Nos. M12294 and M10103), herpes simplex virus (see above), Russian Far East encephalitis, Newcastle disease virus (see above), Venezuelan equine encephalomyelitis (Genbank Acc. No. L044599), rabies (Genbank Acc. No. U11736 and others), vaccinia (EMBL accession X91135) and varicella (GenPept U25806; Russell, 1994, Eur. J. Cancer, 30A, 1165–1171).

Modifications to Membrane Glycoproteins to Obtain Enhanced Induction of Syncytium Formation Certain modifications can be introduced into viral membrane glycoproteins to enhance profoundly their ability to induce the formation of syncytia.

1) Truncation of the cytoplasmic domains of a number of retroviral and herpesvirus glycoproteins has been shown to increase their fusion activity, sometimes with a simultaneous reduction in the efficiency with which they are incorporated into virions (Rein et al, J. Virol. 1994, 68. 1773–1781; Brody et al, J. Virol. 1994, 68, 4620–4627; Mulligan et al, J. Virol. 1992, 66, 3971–3975; Pique et al, J. Virol. 1993, 67, 557–561; Baghian et al, J. Virol. 1993, 67, 2396–2401; Gage et al, J. Virol. 1993, 67, 2191–2201).

2) Transmembrane domain swapping. Transmembrane domain swapping experiments between MLV and HTLV-1 have shown that envelopes which are readily fusogenic in cell-to-cell assays and also efficiently incorporated into virions may not necessarily confer virus-to-cell fusogenicity (Denesvre et al., J. Virol. 1996, 70, 4380–4386).

Modifications to Membrane Glycoproteins to Obtain Enhanced Selectivity of Syncytium Induction 1) Introduction of novel binding specificities into the fusogenic membrane glycoprotein such that the glycoprotein may recognize a selected receptor on a target cell, and thereby to target their fusogenic activities to specific cell types that express the targeted receptors. The fusogenic membrane glycoprotein may be modified so as to be capable of binding to a selected cell surface antigen. The altered glycoprotein may be tissue selective, as any tissue may give rise to a malignancy. Possible target antigens are preferentially expressed on breast, prostate, colon, ovary, testis, lung, stomach, pancreas, liver, thyroid, haemopoietic progenitor, T cells, B cells, muscle, nerve, etc. Additional possible target antigens include true tumor-specific antigens and oncofetal antigens. For example, B lymphocytes are known to give rise to at least 20 different types of haematological malignancy, with potential target molecules including CS10, CD19, CD20, CD21, CD22, CD38, CD40, CD52, surface IgM, surface IgD, idiotypic determinants on the surface of Ig, MHC class II, receptors for IL2, IL4, IL5, IL6, etc. Fusogenic membrane glycoproteins may be modified so as to contain receptor binding components of any ligand, for example, including monoclonal antibodies, naturally occurring growth factors such as interleukins, cytokines, chemokines, adhesins, integrins, neuropeptides, and non-natural peptides selected from phage libraries, and peptide toxins such as conotoxins, agatoxins.

2) Introduction of protease-dependencies into fusogenic viral membrane glycoproteins and thereby to localize the fusogenic activity to specific microenvironments that are rich in the appropriate activating proteases (See "Protease targets" below; see also, Cosset & Russell, Gene Therapy, 1996, 3, 946–956.)

Protease Targets

There appear to be a large number of membrane proteases which are preferentially expressed on the surfaces of tumor cells. They have been implicated in a variety of processes that contribute to disease progression and treatment resistance such as invasion, metastasis, complement resistance.

A) Membrane proteases involved in complement resistance. The human melanoma cell line SK-MEL-170 is resistant to complement-mediated lysis. The molecular basis for this complement resistance has been defined as a membrane protease p65 which rapidly and specifically cleaves C3b deposited on the SK-MEL-170 cell surface (Ollert et al, Cancer Res. 1993, 53, 592–599).

B) Prostate-specific antigen. The proteases present in ejaculated semen are evident in that ejaculated semen is immediately turned into a viscous gel which liquifies within 20 minutes. PSA is a prostatic kallikrein-like serine protease which cleaves the amino acid sequence Tyr-Xaa and participates in this liquefaction process by cleaving semenogelin, the predominant protein in the coagulated part of the ejaculate (Lilja et al, J. Clin. Invest, 1987, 80, 281–285). PSA is produced exclusively by prostatic epithelial cells and is a useful marker for prostatic cancer. PSA has also been shown to cleave IGFBP-3, greatly reducing its affinity for insulin-like growth factor (IGF-1) (Cohen et al., J. Endocrinol. 1994, 142, 407–415). PSA circulating in plasma is inactive because it is bound to serpins but it has been postulated that local release of PSA in metastatic foci of prostatic cancer might lead to the release of IGF1 by cleaving IGFBP binding protein 3 thereby enhancing tumor growth (Cohen et al J. Endocrinol. 1994 Vol. 142 p 407–415).

C) Procoagulant proteases: deposition of fibrin on cancel cells may protect them from the immune system and participation of coagulation enzymes in metastasis has been suggested (Dvorak, Hum. Pathol, 1987, 18, 275–284). Membrane-associated procoagulants which may be of significance in this respect include tissue factor (Edwards et al. Throm. Haemostasis, 1993, 6, 205–213), an enzyme that directly activates factor X (Gordon & Cross, J. Clin. Invest. 1981, 67, 1665–1671), and the activated product of that reaction, factor Xa, which directly converts prothrombin to active thrombin (Seklya et al., J. Biol. Chem. 1994, 269, 32441–32445) by cleaving C-terminal to the sequence Ile-Glu-Gly-Arg (SEQ ID NO:14) after amino acids 327 and 363 of the prothrombin molecule. The protease-sensitive cleavage site PLGLWA (SEQ ID NO:15) is cleaved by GLA and by MT1-MMP, a membrane associated with MMP on human tumor cells (Ye et al., 1995, Biochem. 34:4702; and Will et al., 1996, Jour. Biol. Chem. 271).

D) Plasminogen activation system: plasmin is a broad spectrum trypsin-like protease that degrades fibrin and ECM proteins including laminin, thrombospondin and collagens and that activates other latent matrix-degrading proteases such as collagenases. The expression of protease activity by tumor cells is proposed to facilitate their penetration of basement membranes, capillary walls, and interstitial connective tissues, allowing them to spread to other sites and establish metastases (Dano et al, Adv. Cancer Res. 1985, 44, 139–266). Plasminogen is an abundant plasma protein (Mr=90,000) normally present at a concentration of about 2 μM. Most cell types analyzed, except erythrocytes, have a high density of low affinity (0, 1–2.0 μM) plasminogen binding sites which recognize the lysine binding sites associated with the kringle domains of plasminogen (Redlitz & Plow, Clin. Haem. 1995, 8, 313–327). Cell-bound plasminogen is activated by a single peptide bond cleavage to form plasmin which is composed of a disulfide-linked heavy chain (Mr=60,000, containing five kringle motifs) and light chain (Mr=24,000 containing the seine proteinase catalytic triad). Activation of plasminogen to plasmin is mediated primarily by cell-bound u-PA or t-PA (see below). Cell bound plasmin is more active than soluble plasmin and is resistant to inactivation by the alpha-2-antiplasmin present in serum, but is rapidly inactivated after dissociation from the cell (Stephens et al, J. Cell Biol, 1989, 108, 1987–1995). The protease-sensitive cleavage site in plasminogen is Arg-Val at positions 580 and 581; cleavage occurs between the two residues.

E) Plasminogen Activators. Urokinase plasminogen activator (u-PA) is involved in cell-mediated proteolysis during wound healing, macrophage invasion, embryo implantation, signal transduction, invasion and metastasis. Pro-uPA is usually released by cells as a single-chain of 55 kDa (scuPA), and binds to its GPI-anchored cellular receptor (uPAR—Kd 0.05–3.0 nM) where it is efficiently converted to its active (two-chain) form by plasmin or other protease. Thrombin inactivates the active form of u-PA (Ichinose et al, J. Biol. Chem. 1986, 261, 3486–3489). The activity of cell-bound u-PA is regulated by three inhibitors, PAI-1, PAI-2 and protease nexin (PN) which can bind to the cell-bound enzyme resulting in its endocytic sequestration from the cell surface (Conese and Blasi, Clin. Haematol. 1995, 8, 365–389).

In cancer invasion there appears to be a complex interplay between the various components of the plasmin-plasminogen activator system. uPAR clustering on the cell surface serves to focus the process of plasmin-mediated pericellular proteolysis at the invading front of the tumor. pro-u-PA, uPAR, PAI-1 and PAI-2 can be produced in varying amounts by the cancer cells, or by nontransformed stromal cells at the site of tumor invasion and their production by these different cell types can be regulated by a variety of stimuli (Laug et al, Int. J. Cancer, 1992, 52, 298–304; Ciambrone & Mckeown-Longo, J. Biol. Chem. 1992, 267, 13617–13622; Kessler & Markus, Semin. Thromb. Haemostasis, 1991, 17, 217–224; Lund et al, EMBO J., 1991, 10, 3399–3407). Thus, various different cell types can contribute to the assembly on the tumor cells of all the components of the proteolytic machinery that is required for matrix destruction.

F) Trypsin-like proteases: tumor-associated trypsin inhibitor (TATI) is a 6-kDa protease inhibitor whose levels are elevated in patients with advanced cancer (Stenman et al, Int. J. Cancer, 1982, 30, 53–57). In search of the target protease for the TATI, two trypsin-like proteases have been purified from the cyst fluid of mucinous ovarian tumors (Koivunen et al, J. Biol. Chem. 1989, 264, 14095–14099). Their substrate specificities were found to be very similar to those of pancreatic trypsins 1 and 2 and they were found to be efficient activators of pro-urokinase but could not activate plasminogen directly. Trypsin cleaves C-terminal to Lys or Arg residues.

G) Cathepsin D: this is a pepstatin-sensitive, lysosomal aspartyl protease which is secreted in large amounts by breast cancer cells and by a variety of other cancer cell types. Purified cathepsin D and conditioned medium from cathepsin D-secreting cells have been shown to degrade extracellular matrix at pH 4.5, but not at neutral pH (Briozzo et al, Cancer Res. 1988, 48, 3688–3692). It has therefore been proposed that the enzyme may be an important facilitator of tumor invasion when it is released into an acidic (pH<5.5) microenvironment. One factor distinguishing it from other protease classes is that it can act at a distance from the cancer cell after it has been secreted.

H) Cathepsin B, L: leupeptin-sensitive lysosomal cysteinyl proteases which act at acidic pH. These and other cathepsins, such as cathepsin D (above), are dipeptidylpeptide hydrolases, which cleave adjacent to certain dipeptides. For example, cathepsin B is a dihistidyl carboxypeptidase.

Methods of Treating a Cell Proliferative Disorder According to the Invention

The invention contemplates treatment of cell proliferative disorders using a syncytium-inducing polypeptide to induce syncytium formation of unwanted cells. Cell proliferative disorders include treatment of malignant diseases, as in cancer gene therapy, as well as diseases involving immunosuppression wherein unwanted lymphocytes proliferate, as in rheumatoid arthritis, or wherein unwanted keratinocytes (skin cells) proliferate, as in psoriasis.

The primary target cells in which the syncytium-inducing polypeptide is expressed (index cells) can be stationary cells (e.g. the neoplastic cells or stromal elements in a solid tumor) or migratory cells (e.g. T lymphocytes, B lymphocytes and other haemopoietic cells or migratory neoplastic cells in haematological malignancies).

The secondary target cells (with which the syncytium-inducing polypeptide-expressing target cells will fuse) may likewise be stationary or migratory.

The target cells can be transduced ex vivo or in vivo by the syncytium-inducing polypeptide-encoding vectors. Any vector system, whether viral or nonviral can be used to deliver a gene or genes encoding a syncytium-inducing polypeptide to the target cells. Targeting elements may be included in the vector formulation to enhance the accuracy of gene delivery to the target cells and tissue/tumor-selective regulatory elements can be included in the vector genome to ensure that the expression of a gene or genes encoding a syncytium-inducing polypeptide is restricted to the chosen target cells.

Genes encoding syncytium-inducing polypeptides could therefore be used in various ways for therapeutic benefit. The aim in all cases is to destroy unwanted target cells by causing them to fuse with syncytium-inducing polypeptide-expressing index cells. The initial targets for gene transfer are therefore the index cells, but the ultimate targets of the therapeutic strategy are the cells with which they fuse. Many different therapeutic strategies can be envisaged.

For example, where the aim of the protocol is to destroy neoplastic cells in the patient, the index cells need not be neoplastic. Migratory T lymphocytes expressing tumor-selective syncytium-inducing polypeptides might form syncytia exclusively with neoplastic cells. Local expression of tumor-selective (or, less optimally, nonselective) syncytium-inducing polypeptides in the stromal, vascular endothelial or neoplastic cells in solid tumors might lead to recruitment of neighboring neoplastic cells into syncytia.

For leukemias and other haematogenous malignancies, expression of leukemia-selective syncytium-inducing polypeptides in vascular endothelium or stromal bone marrow cells might lead to recruitment of circulating leukaemic cells into stationary syncytia. Alternatively, expression of leukaemia-selective syncytium-inducing polypeptides in circulating T cells or in the leukaemic cells themselves might allow these cells to nucleate the formation of leukaemic cell syncytia in heavily infiltrated tissues, or lead to recruitment of leukaemic cells into recirculating syncytia. Another method of determining whether the inventive treatment methods are successful is to perform a biopsy of tissue that is targeted for syncytium formation, and to observe cells of the tissue in a microscope for formation of syncytia.

How to Determine Induction of Syncytium Formation According to the Invention

Induction of syncytium formation may be determined in vitro as described herein. Syncytium formation in vivo is determined via tissue biopsy from a candidate patient treated according to the invention, wherein under direct visualization large multinucleate areas are observed in a tissue section.

Dosage, Pharmaceutical Formulation and Administration

A vector containing a gene encoding a syncytium-inducing polypeptide according to the invention may be administered directly to a patient or may be administered utilizing an ex vivo approach whereby cells are removed from a patient or donor, transduced with the vector containing a therapeutic nucleic acid sequence encoding a syncytium inducing polypeptide and reimplanted into the patient. A vector or host cells containing a particular therapeutic nucleic acid sequence encoding a syncytium-inducing polypeptide according to the invention can be administered prophylactically, or to patients having a cell proliferative disease or condition treatable by supplying and expressing the gene encoding the syncytium-inducing polypeptide by means of an appropriate delivery vehicle, e.g., a liposome, by use of iontophoresis, electroporation and other pharmacologically approved methods of delivery. Routes of administration may include intramuscular, intravenous, aerosol, oral (tablet or pill form), topical, systemic, ocular, as a suppository, intraperitoneal and/or intrathecal.

Some methods of delivery that may be used include: viral or non-viral vector delivery of a DNA, encapsulation in liposomes, transfection of cells ex vivo with subsequent reimplantation or administration of the transfected cells.

Viral vectors that can be used to deliver foreign nucleic acid into cells include but are not limited to retroviral vectors, adenoviral vectors, adeno-associated viral vectors, herpesviraul vectors, and Semliki forest viral (alphaviral) vectors. Defective retroviruses are well characterized for use in gene transfer for gene therapy purposes (for a review see Miller, A. D. (1990) *Blood* 76:271). Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are well known to those skilled in the art. Adeno-associated virus (AAV) is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). An AAV vector such as that described in Tratschin et al. (1985) *Mol. Cell. Biol.* 5:3251–3260 can be used to introduce nucleic acid into cells. A variety of nucleic acids have been introduced into different cell types using AAV vectors (see for example Hermonat et al. (1984) *Proc. Natl. Acad. Sci. USA* 81:6466–6470; and Tratschin et al. (1985) *Mol. Cell. Biol.* 4:2072–2081).

Other types of delivery strategies useful in the present invention, include: injection of naked DNA, injection of charge modified DNA, or particle carrier drug delivery vehicles. Unmodified nucleic acid sequences, like most small molecules, are taken up by cells, albeit slowly. To enhance cellular uptake, the vector containing a sequence encoding a syncytium-inducing polypeptide may be modified in ways which reduce its charge but will maintain the expression of specific functional groups in the final translation product. This results in a molecule which is able to diffuse across the cell membrane, thus removing the permeability barrier.

Chemical modifications of the phosphate backbone will reduce the negative charge allowing free diffusion across the membrane. This principle has been successfully demonstrated for antisense DNA technology which shows that this is a feasible approach. In the body, maintenance of an external concentration will be necessary to drive the diffusion of the modified nucleic acid sequence into the cells of the tissue. Administration routes which allow the tissue to be exposed to a transient high concentration of the nucleic acid sequence encoding a syncytium-inducing polypeptide, which is slowly dissipated by systematic adsorption are preferred. Intravenous administration with a carrier designed to increase the circulation half-life of the nucleic acid sequence can be used. The size and composition of the carrier restricts rapid clearance from the blood stream. The carrier, made to accumulate at the desired site of transfer, can protect the nucleic acid sequence from degradative processes.

Delivery vehicles are effective for both systematic and topical administration. They can be designed to serve as a slow release reservoir, or to deliver their contents directly to the target cell. An advantage of using direct delivery vehicles is that multiple molecules are delivered per uptake. Such vehicles have been shown to increase the circulation half-life of drugs which would otherwise be rapidly cleared from the blood stream. Some examples of such specialized drug delivery vehicles which fall into this category are liposomes, hydrogels, cyclodextrins, biodegradable nanocapsules, and bioadhesive microspheres.

From this category of delivery systems, liposomes are preferred. Liposomes increase intracellular stability, increase uptake efficiency and improve biological activity. Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver nucleic acids to cells and that the nucleic acid remains biologically active. For example, a liposome delivery vehicle originally designed as a research tool, Lipofectin, has been shown to deliver intact mRNA molecules to cells yielding production of the corresponding protein. Liposomes offer several advantages: They are non-toxic and biodegradable in composition; they display long circulation half-lives; and recognition molecules can be readily attached to their surface for targeting to tissues. Finally, cost effective manufacture of liposome-based pharmaceuticals, either in a liquid suspension or lyophilized product, has demonstrated the viability of this technology as an acceptable drug delivery system.

Other controlled release drug delivery systems, such as nanoparticles and hydrogels, may be potential delivery vehicles for a nucleic acid sequence encoding an episomal vector containing a therapeutic nucleic acid sequence or sequences. These carriers have been developed for chemotherapeutic agents and protein-based pharmaceuticals, and consequently, can be adapted for nucleic acid delivery.

DNA, cells or proteins according to the invention may also be systematically administered. Systemic absorption refers to the accumulation of drugs in the blood stream followed by distribution throughout the entire body. Administration routes which lead to systemic absorption include: intravenous, intramuscular, subcutaneous, intraperitoneal, intranasal, intrathecal and ophthalmic. Each of these administration routes exposes the nucleic acid sequence encoding a syncytium inducing polypeptide to an accessible targeted tissue. Subcutaneous administration drains into a localized lymph node which proceeds through the lymphatic network into the circulation. The rate of entry into the circulation has been shown to be a function of molecular weight or size. Liposomes injected intravenously show accumulation in the liver, lung and spleen. The composition and size can be adjusted so that this accumulation represents 30% to 40% of the injected dose. The remaining dose circulates in the blood stream for up to 24 hours.

The dosage will depend upon the disease indication and the route of administration but should be between 1–1000 μg of DNA or protein/kg of body weight/day or 10,000–100,000 transfected cells/day. The duration of treatment will extend through the course of the disease symptoms, possibly continuously. The number of doses will depend upon disease delivery vehicle and efficacy data from clinical trials.

Where a syncytium-inducing polypeptide is administered, via DNA encoding the polypeptide or via a host cell containing the DNA or via the protein itself, in a pharmaceutical formulation, the formulation may be mixed in a physiologically acceptable diluent such as water, phosphate buffered saline, or saline, and will exclude cell culture medium, particularly culture serum such as bovine serum or fetal calf serum, <0.5%.

The following examples are offered by way of illustration and are not intended to limit the invention in any manner.

Exemplification

The following examples demonstrate the preparation and testing of therapeutic uses of genes encoding (targeted) fusogenic membrane glycoproteins for gene therapy of cancer. The examples specifically describe the preparation of a retroviral vector and retroviral vector stock containing genes encoding measles virus F and H glycoproteins, the use of these vectors to induce syncytium formation between HF-transduced murine fibroblasts and nontransduced human tumor cells, and administration of the transduced fibroblasts to tumor-bearing mice to reduce tumor growth.

When expressed concurrently in the same cell, measles virus F and H glycoproteins can mediate cell-cell fusion with neighboring cells, provided the neighboring cells express the measles virus receptor (CD46). Human cells express the CD46 measles virus receptor, whereas murine cells do not. In the experiments described below, a retroviral vector capable of transferring the measles virus F and H genes is used to demonstrate the therapeutic potential of gene therapy vectors encoding targeted or nontargeted fusogenic viral membrane glycoproteins for cancer therapy. The vectors can be used for direct gene transfer to tumor cells or for transduction of nontumor cells which are then employed for their selective antitumor effect.

EXAMPLE 1

1.1 Construction of Retroviral Vector Plasmid Coding for Measles Virus F and H Glycoproteins.

Figure 1:

The plasmid shown schematically in FIG. 1 (not to scale) is constructed using standard cloning methods. In relation to FIG. 1, LTR=Moloney murine leukaemia virus long terminal repeat; ?=Moloney murine leukaemia virus packaging signal; IRES poliovirus internal ribosome entry site; H=measles virus H glycoprotein coding sequence; F=measles virus F glycoprotein coding sequence; PHLEO= phleomycin resistance marker; the dotted line represents the vector backbone (either pUC or pBR322-based). In brief, the coding sequence of the measles virus H gene is cloned from pCGH5 (Cathomen et al, 1995, Virology, 214, 628–632), into the NotI site of the retroviral vector plasmid pGCP (which contains the poliovirus internal ribosome entry site flanked by NotI and ClaI cloning sites). The measles virus F gene is then cloned from pCGF (Cathomen et al, 1995, Virology, 214, 628–632) into the ClaI site of the same vector, 5' of the internal ribosome entry site to produce the vector named pHF. A phleomycin selectable marker gene is then introduced into the vector 5' of the 5' LTR.

1.2 Preparation of Retroviral Vector Stocks.

The plasmid pHF is transfected into amphotropic retroviral packaging cell lines which were derived from murine fibroblasts. Suitable packaging cell lines are widely available and include the NIH3T3-derived cell lines PA317 and GP+env AM12. Stably transfected packaging cells are selected in phleomycin 50 ug/ml and used as a source of HF retroviral vectors capable of efficiently transferring the measles virus F and H genes to human and murine target cells.

1.3 Transduction of Transplantable Human Tumor Cell Lines Leading to Formation of Multinucleated Syncytia Through the Induction of Cell-Cell Fusion.

The HF retroviral vector stocks are used to transduce a panel of human tumor cell lines which are subsequently observed for the formation of multinucleated syncytia, expected to be maximal 24 to 72 hours after retroviral transduction of the cells. The tumor cell lines are grown to near-confluency before transduction. Examples of tumor cell lines that can be used for this assay are A431 (epidermoid carcinoma), HT 1080 (fibrosarcoma), EJ (bladder carcinoma), C175 (colon carcinoma), MCF7 (breast carcinoma), HeLa (cervical carcinoma), K422 (follicular lymphoma), U266 (myeloma). Most, if not all, of the human tumor cell lines tested undergo extensive cell-cell fusion shortly after transduction with the HF retroviral vector.

1.4 Inoculation of Nude Mice with Transplantable Human Tumor Cell Lines and Subsequent in vivo Transfer of H and F Genes to the Tumor Deposits: Demonstration that Fusogenic Membrane Glycoproteins Mediate Tumor Destruction in the Absence of a Functional Immune System.

Mice are challenged by subcutaneous inoculation into the flank with $10^7$ human tumor cells. Suitable cell lines for use in these experiments are listed above in Section 3. Between one and fourteen days after subcutaneous inoculation with tumor cells, the growing tumor xenografts are inoculated with concentrated HF retroviral vector stocks or by control vector stocks encoding either measles F or measles H glycoproteins. Tumor growth is slowed or completely inhibited by HF retroviral vector inoculation but not by inoculation of control (H or F alone) vectors.

1.5 Transduction of Murine Fibroblasts; Lack of Cell-Cell Fusion and Absence of Multinucleated Syncytia.

The HF retroviral vector stocks are used to transduce murine NIH3T3 fibroblasts which are subsequently observed for the formation of multinucleated syncytia. No cell-cell fusion occurs and no multinucleated syncytia are observed.

1.6 Mixing of HF-Transduced Murine Fibroblasts with Nontransduced Human Tumor Cells Leading to the Formation of Multinucleated Syncytia Through the Induction of Cell-Cell Fusion Between HF-Transduced Murine Fibroblasts and Nontransduced Human Tumor Cells.

The HF retroviral vector stocks are used to transduce murine N1H3T3 fibroblasts which are subsequently mixed, at various ratios from 1:1 to 1:10,000, with nontransduced human tumor cell lines. The mixed cell populations are then plated at high density and observed for the formation of multinucleated syncytia. Cell-cell fusion occurs between HF-transduced N1H3T3 fibroblasts and nontransduced human tumor cells leading to the formation of multiple hybrid syncytia, each one nucleating on a transduced NIH3T3 cell. Syncytia are not observed in control cultures in which nontransduced N1H3T3 cells are mixed with nontransduced human tumor cells.

1.7 Inoculation of Nude Mice with Mixtures of HF-Transduced Murine Fibroblasts and Nontransduced Human Tumor Cells: Demonstration that Fusogenic Membrane Glycoproteinexpressing Cells Mediate Tumor Destruction by Recruitment into Syncytia of Nontransduced Human Tumor Cells.

The HF retroviral vector stocks are used to transduce murine NIH3T3 fibroblasts which are subsequently mixed, at varying ratios from 1:1 to 1:10,000, with nontransduced human tumor cell lines. Mixed cell populations containing $10^7$ tumor cells admixed with from $10^3$ to $10^7$ HF-transduced NIH3T3 cells are then inoculated subcutaneously into the flanks of nude (BALBC nu/nu) mice and the mice are monitored for the growth of subcutaneous tumors whose diameters are recorded daily. Control mice are challenged with $10^7$ nontransduced human tumor cells. Tumor growth is slowed or completely inhibited by admixed HF-transduced NIH3T3 fibroblasts which express the measles virus F and H glycoproteins, but not by admixed nontransduced NIH3T3 fibroblasts.

A composition according to the invention is determined to be useful according to treatment methods of the invention wherein tumor growth (e.g., malignant tumor growth) is reduced to the extent that the tumor remains the same size (i.e., does not increase by weight or measurement) or the tumor is reduced in weight or size by at least 25% in an animal model of the cancer (e.g., the nude mouse model described above) or in a patient. Those compositions which are particularly useful according to the invention will confer tumor reduction of at least 50%.

Alternatively, a tissue biopsy is performed in order to observe syncytium formation via direct visualization. A composition according to the invention also is determined to be useful according to treatment methods of the invention wherein syncytium formation is observed to the extent that multinucleate areas of cytoplasm are observed in a tumor tissue biopsy during the course of treatment.

EXAMPLE 2

Display of EGF and IGF on Measles H Glycoprotein

Materials and Methods
Plasmid Construction

Unmodified Measles Virus (MV) F and MV H protein were encoded by the expression plasmids pCG-F and pCG-H, respectively (Catomen et al, Virology 214 p628, 1995). To make the chimeric MV H expression constructs, first the SfiI site in pCG-H was deleted, so that we could introduce our displayed ligands as SfiI/NotI fragments. This was done by digesting pCG-H with SfiI, endfilling the cohesive ends using Klenow fragment of *E. coli* DNA polymerase and dNTPs, then re-ligating the purified product. This construct was tested to check that it was still functional in cell fusion assays (see later). We could now make constructs which would enable us to insert ligands as SfiI/NotI fragments. To make the construct pCG-H SfiI/NotI, which introduces the SfiI/NotI cloning site at the C-terminus of the MV H sequence, oligonucleotides HXmabak (5'-CCG GGA AGA TGG AAC CAA TGC GGC CCA GCC GGC CTC AGG TTC AGC GGC CGC ATA GTA GA-3', Seq ID No. 1) and HSpefor (5'-CTA GTC TAC TAT GCG GCC GCT GAA CCT GAG GCC GGC TGG GCC GCA TTG GTT CCA TCT TC-3', Seq ID No. 2) were made. When annealed together these two oligonucleotides form a DNA fragment with XmaI and SpeI cohesive ends. This fragment was ligated to the XmaI/SpeI digested pCG-H(Sfi-) backbone. The correct sequence of the construct was verified by DNA sequencing.

To make the construct pCG-H FXSfiI/NotI, where there is a FXa protease cleavage signal before the SfiI/NotI cloning sites at the C-terminus of the MV H sequence, oligonucleotides HXmaFXbak (5'-CCG GGA AGA TGG AAC CAA TAT CGA GGG AAG GGC GGC CCA GCC GGC CTC AGG TTC AGC-3', Seq ID No. 3) and HNotFXfor (5'-GGC CGC TGA ACC TGA GGC CGG CTG GGC CGC CCT TCC CTC GAT ATT GGT TCC ATC TTC-3', Seq ID No. 4) were made. When annealed together these two oligonucleotides form a DNA fragment with XmaI and NotI cohesive ends. This fragment was ligated to the XmaI/NotI digested pCG-H SfiI/NotI backbone. The correct sequence of the constructs was verified by DNA sequencing. Constructs pCG-H $EGF^{R-}$, pCG-H $XEGF^{R-}$, pCG-H IGF and pCG-H XIGF were made by transferring the SfiI/NotI EGF and IGF fragments from $pEGF^{R-}$GS1A1 (Peng, PhD Thesis) and pIGFA1 (IA) (WO97/03357, Russell et al.) respectively into SfiI/NotI digested pCG-H SfiI/NotI and pCG-H FXSfiI/NotI. FIG. 2 shows a diagrammatic representation of the four constructs.

To enable us stably to express the chimeric H proteins in mammalian cells, we need to have a selectable marker in the expression construct. This was achieved by transferring the whole MV H gene with the SfiI/NotI cloning site at its C-terminus into the envelope expression construct, EMo1 (Cosset et al, J. Virol. 69 p6314, 1995). So, to make pFBH SfiI/Not, pCG-H SfiI/Not was cut with ClaI and SpeI to release the H gene with the SfiI/NotI cloning site and EMo1 was cut with XbaI and ClaI to remove EGF and the Mo envelope sequence giving us the backbone. The cohesive ends of both fragments were endfilled using Klenow fragment of *E. coli* DNA polymerase and dNTPs. The backbone was phosphatased and the purified fragments were ligated together. The construct was checked by diagnostic digests for the correct orientation. To make the construct pFBH FXSfI/Not, pCG-H FXSfiI/Not was cut with NsiI and NotI to release part of the H sequence with a FXa protease cleavage signal and the SfiI/NotI cloning site at its C-terminus. pFBH SfiI/Not was also cut with NsiI and NotI to give us the backbone, and the two fragments were ligated together. The construct was checked by sequencing for correctness. Constructs pFBH $EGF^{R-}$, pFBH $XEGF^{R-}$, pFBH IGF and pFBH XIGF were made by transferring the SfiI/NotI EGF and IGF fragments from $pEGF^{R-}$GS1A1 and pIGFA1 respectively into SfiI/NotI digested pFBH SfiI/Not and pFBH FXSfiI/NotI. FIG. 3 shows a diagrammatic representation of the four constructs. To make the construct pFBH, where there is no C-terminal extension, pCG-H was cut with ClaI and SpeI to release the H gene and EMo1 was cut with XbaI and ClaI to remove EGF and the Mo envelope sequence giving us the backbone. The cohesive ends of both fragments were endfilled using Klenow fragment of E. coli DNA polymerase and dNTPs. The backbone was phosphatased and the purified fragments were ligated together. The construct was checked by diagnostic digests for the correct orientation.

Cell Lines

C170 cells, a human colon cancer cell line (Durrant et al, Br. J. Cancer 53 p37, 1986), and Human A431 cells (ATCC CRL1555) were grown in DMEM supplemented with 10% fetal calf serum. To enable easy detection of cell-cell fusion the C170 and A431 cells were infected with A viral supernatant, harvested from TELCeB6 producer cells (Cosset et al, J. Virol. 69 p6314, 1995), which transfers a gene coding for β-galactosidase tagged with a nuclear localisation signal. Single colonies of cells were grown up and clones that stained blue were picked. These blue staining C170 and A431 cells were used in cell fusion assays. The different MV H expression constructs pFBH, pFBH EGF$^{R-}$, pFBH XEGF$^{R-}$, pFBH IGF and pFBH XIGF (5 mg DNA) were transfected into TELCeB6 cells (Cosset et al, J. Virol. 69 p7430, 1995) using 30 ml Superfect (Qiagen). Stable phleomycin (50 mg/ml) resistant colonies were expanded and pooled. Cells were grown in DMEM supplemented with 10% fetal calf serum.

Immunoblots

To obtain cell lysates, TELCeB6 cells stably transfected with the MV H constructs were lysed in a 20 mM Tris-HCl buffer (pH 7.5) containing 1% Triton X-100, 0.05% SDS, 5 mg/ml sodium deoxycholate, 150 mM NaCl and 1 mM phenylmethylsulfonylfluoride. Lysates were incubated for 10 mins at 4° C. and then centrifuged for 10 mins at 10,000×g to pellet the unwanted nuclei. Aliquots of the cell lysates (50 μl) were then separated on a 10% polyacrylamide gel under reducing conditions followed by transfer of the proteins onto nitrocellulose paper (NC) (Amersham). The NC was blocked with 5% skimmed milk powder (Marvel) in PBS-0.1% Tween 20 (PBST) for 30 mins at room temperature. The MV H proteins were detected by incubating the NC for 3 hours with a MV H specific rabbit serum (1 in 3000) which was raised against a peptide derived from the amino terminus of the H protein (kind gift from Roberto Cattaneo, University of Zurich). After extensive washing with PBST the NC was incubated with horseradish peroxidase-conjugated swine anti-rabbit antibodies (1 in 3000) (DAKO, Denmark) for 1 hour at room temperature. Proteins were visualised using the enhanced chemiluminescence kit (Amersham Life Science, UK).

Cell-Cell Fusion Assays

Blue staining C170 and A431 cells were seeded at 5×10$^5$ cells/well in six-well plates and incubated at 37° C. overnight. MV H expression constructs, pCG-H, pCG-H EGF$^{R-}$, pCG-H XEGF$^{R-}$, pCG-H IGF and pCG-H XIGF, were co-transfected into the C170 and A431 cells along with the MV F expression construct, pCG-F. Transfections were carried out using 2.5 mg of the relevant plasmids and 15 ml Superfect. After transfection the cells were incubated with regular medium for 48–72 hrs, until syncytia could be clearly seen. X-Gal staining for detection of β-galactosidase activity was performed as previously described (Takeuchi et al., 1994). Fusion efficiency was scored (− no syncytia, + definite syncytia, ++ abundant syncytia).

Results

Construction of Chimeric MV H Expression Constructs

Figure 2:
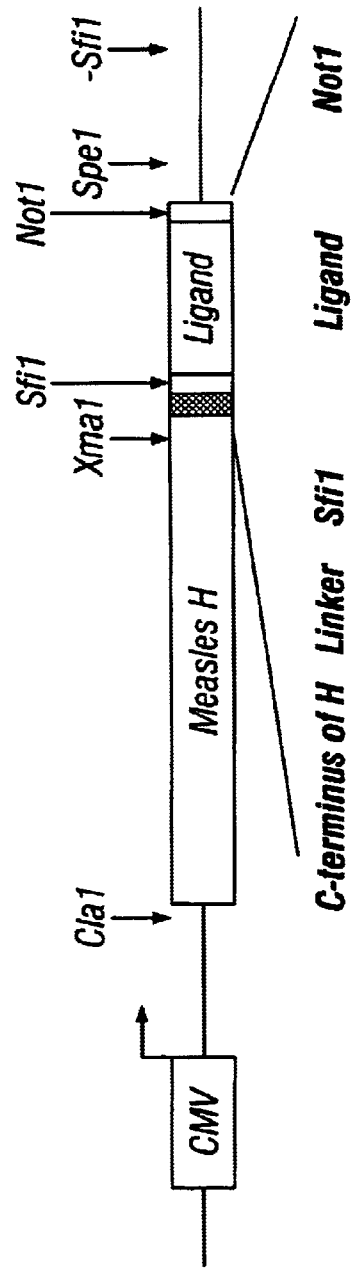
Figure 3:
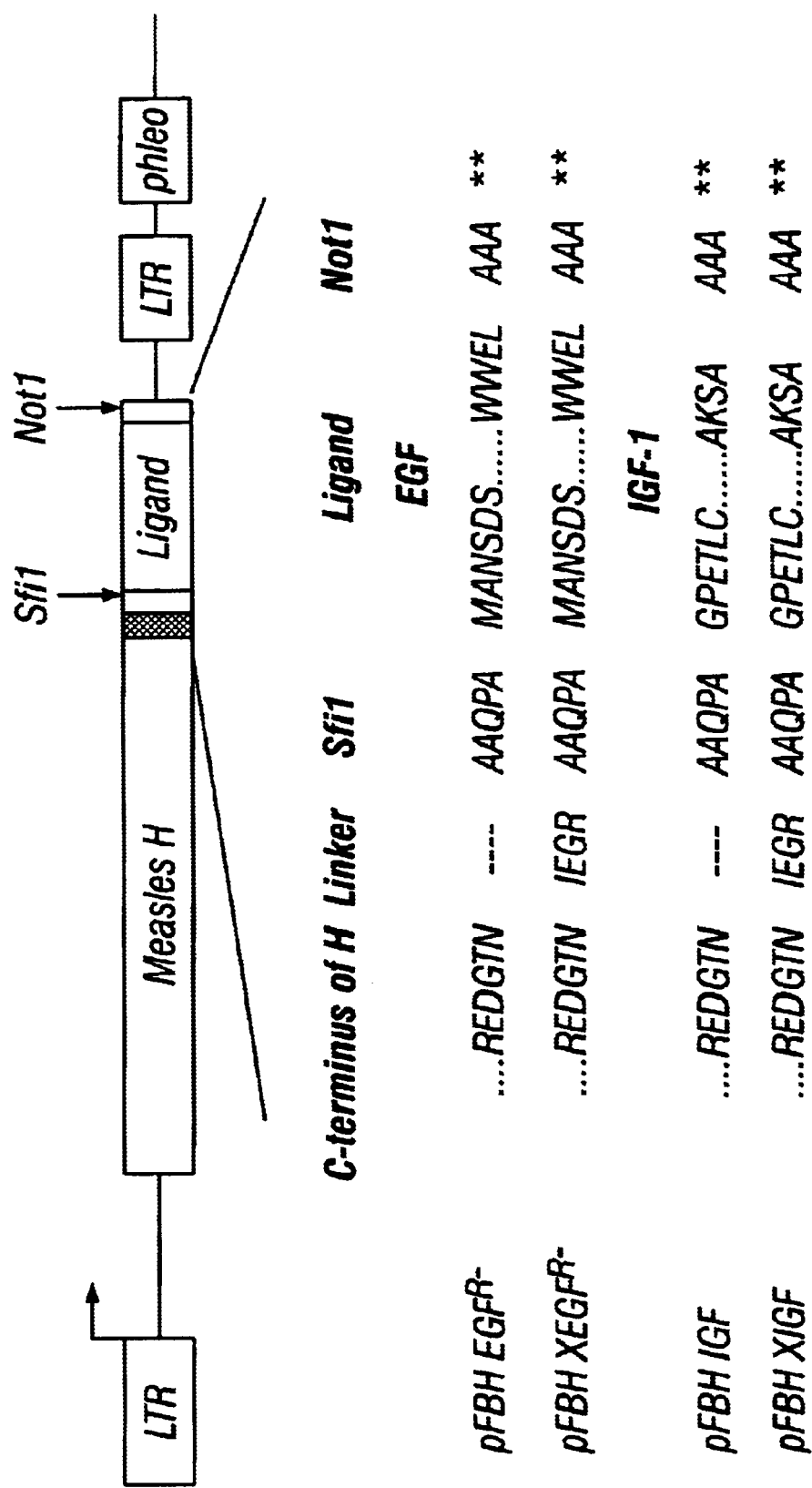
Figure 4:
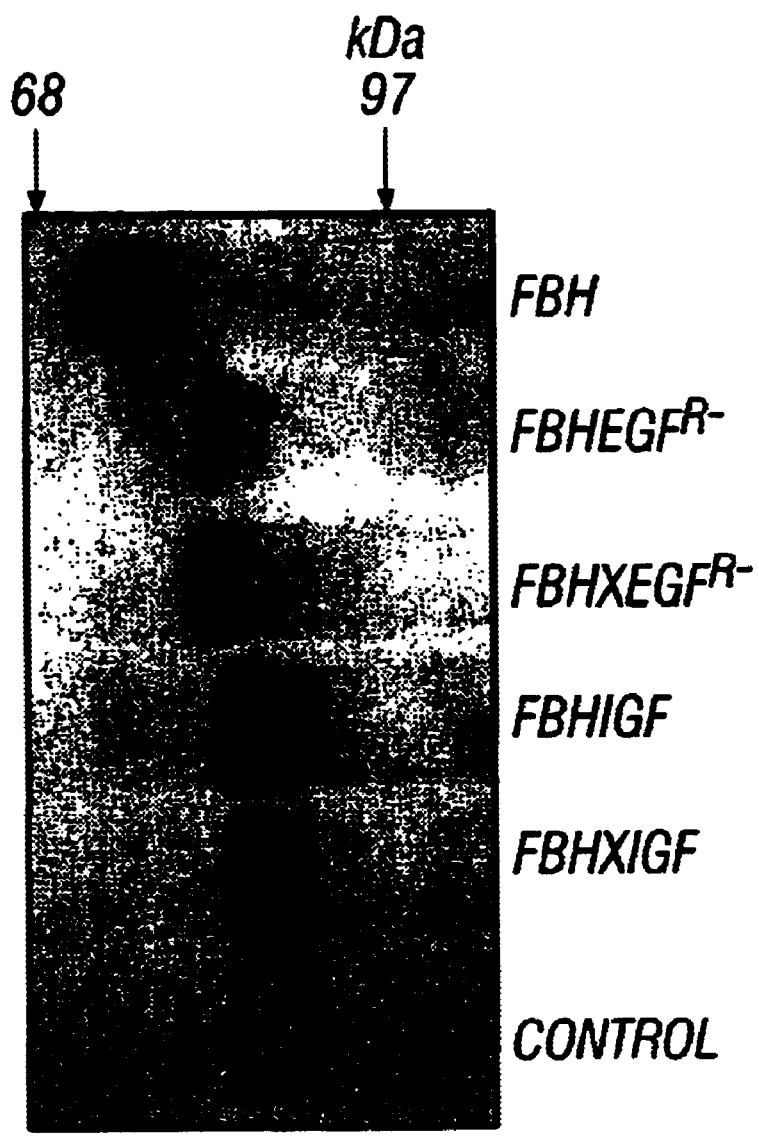
FIG. 4 is an immunoblot of cell lysates prepared from TELCeB6 transfectants, pFBH, pFBH EGFR$^{R-}$, pFBH XEGF$^{R-}$, pFBH IGF, pFBH XIGF and the control, untransfected TELCeB6, probed with an anti-MV H antiserum.

A series of expression constructs were made which code for chimeric MV H proteins in which the ligands EGF and IGF are fused at the C-terminus of the H protein with or without a Factor Xa-cleavable linker (FIGS. 2 and 3). FIG. 2 shows constructs which are driven by the CMV promoter, but these constructs contain no selectable marker for selection in mammalian cells. Expression of the constructs in FIG. 3 is driven by a retroviral LTR and these constructs contain the selectable marker, phleomycin, for selection in mammalian cells Expression of the Chimeric MV H Proteins The different MV H expression constructs, pFBH, pFBH EGF$^{R-}$, pFBH XEGF$^{R-}$, pFBH IGF and pFBH XIGF were stably transfected into TELCeB6 cells. Immunoblots were performed on cell lysates prepared from these stable TELCeB6 transfectants. FIG. 4 shows that all chimeric MV H proteins are expressed to a comparable level to that of the wild type MV H protein. Moreover, the blot shows that the displayed domains are not spontaneously cleaved from the chimeric MV H glycoproteins.

Figure 5:
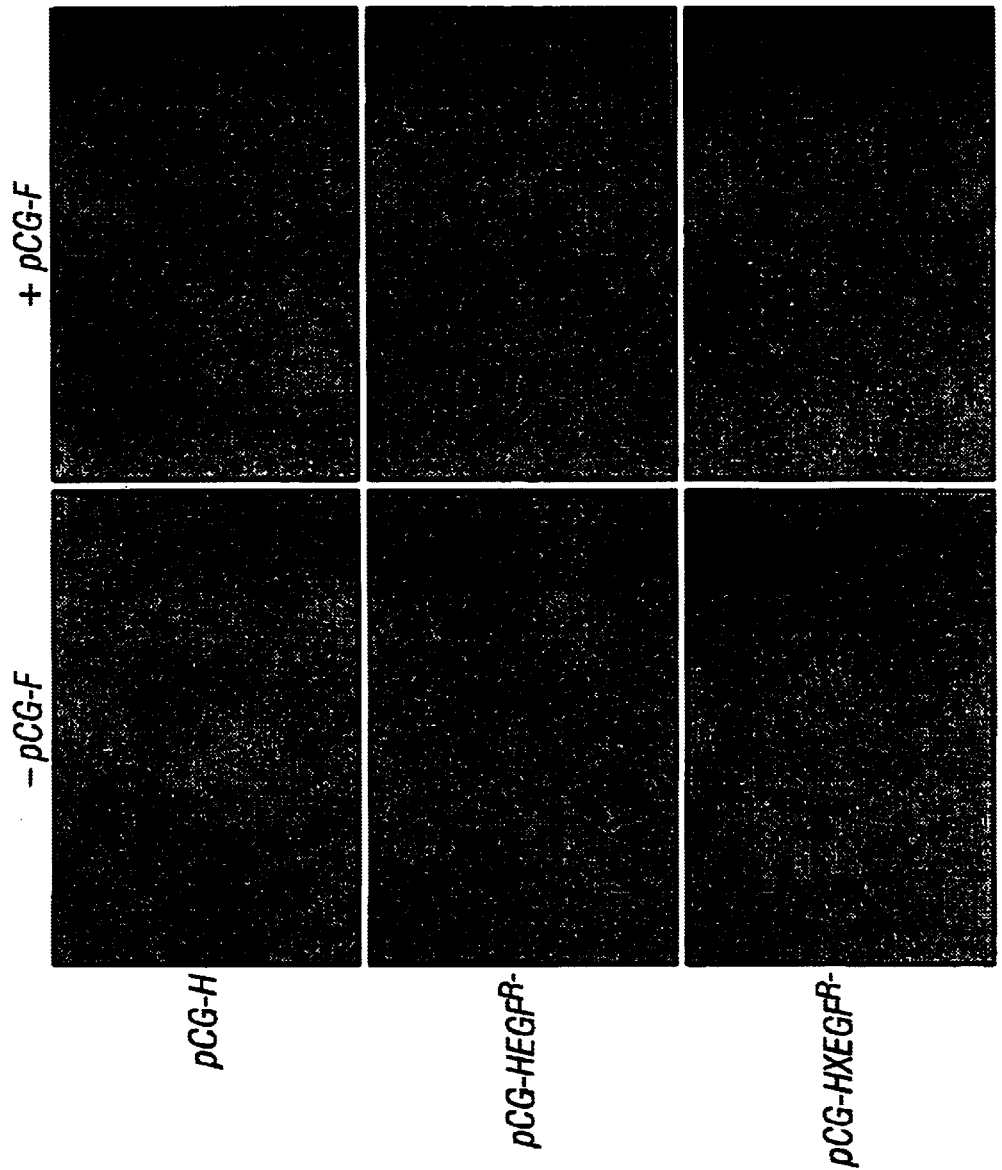
FIG. 5 shows a magnified view showing large C170 syncytia in a cell-cell fusion assay after X-gal staining: chimeric MV H proteins show syncytia formation, although at a lower level to that of the unmodified H protein.

Cell-Cell Fusion Assays MV H expression constructs, pCG-H, pCG-H EGF$^{R-}$, pCG-H XEGF$^{R-}$, pCG-H IGF and pCG-H XIGF, were co-transfected into the β-galactosidase expressing C170 and A431 cells along with the MV F expression construct, pCG-F. The cells were stained with X-gal substrate 72 hrs after transfection to allow ease of cell-cell fusion detection. Results of the assays are shown in Tables 1 and 2 and in FIG. 5. The chimeric MV H proteins were potent inducers of cell-cell fusion in C170 cells although their potency was slightly reduced compared to the unmodified H protein (Table 1, FIG. 5). Cell-cell fusion in A431 was abolished for the chimeric H proteins compared to the unmodified MV H protein which was a potent inducer of cell-cell fusion (Table 2).

The results show that:

1) Foreign polypeptides can be displayed as fusions to the extreme C-terminus of the MV H protein.
2) The chimeric H glycoproteins are efficiently expressed and are functional in cell-cell fusion assays.
3) The displayed ligand can target the specificity of cell-cell fusion.

TABLE 1

This table shows the results of cell-cell fusion on β-galactosidase expressing C170 cells. Chimeric MV H proteins are potent inducers of cell-cell fusion when co-expressed with unmodified F glycoproteins.
− = no syncytia, + = definite syncytia, + + = abundant syncytia.

|  | −pCG-F | +pCG-F |
|---|---|---|
| pCG-H | − | + + |
| pCG-H EGF | − | + + |
| pCG-H XEGF | − | + + |

TABLE 2

This table shows the results of cell-cell fusion assay on β-galactosidase expressing A431 cells. The unmodified MV H protein is a potent inducer of cell-cell fusion when co-expressed with unmodified F glycoproteins. However, chimeric MV H proteins show no syncytia formation. − = no syncytia, + = definite syncytia, + + = abundant syncytia.

|  | −pCG-F | +pCG-F |
|---|---|---|
| pCG-H | − | + + |
| pCG-H EGF | − | − |
| pCG-H XEGF | − | − |

EXAMPLE 3
Demonstration that GALV Envelope with Truncated Cytoplasmic Tail is Hyperfusogenic on Human Tumour Cell Lines

Materials and Methods
Plasmids Used

The expression constructs of Measles Virus (MV) F and MV H protein were encoded by the expression plasmids pCG-F and pCG-H, respectively (Catomen et al, Virology 214 p628, 1995). FBdelPGASAF encodes the wildtype GALV envelope and FBdelPGASAF-fus encodes a C-terminally truncated GALV envelope lacking the cytoplasmic tail (see attached sequence, FIG. 6).

Cell Lines

Human C170 (Durrant et al, Br. J. Cancer 53 p37, 1986), Human A431 cells (ATCC CRL1555), Human TE671 (ATCC CRL8805), Human Hela (ATCC CCL2), and the murine cell line NIH3T3 were grown in DMEM supplemented with 10% fetal calf serum. All of these cell lines, except NIH3T3 have receptors for the GALV envelope and for the MV H glycoprotein.

Cell-Cell Fusion Assays

Cells were seeded at $5 \times 10^5$ cells/well in six-well plates and incubated at 37° C. overnight. The fusogenic and non-fusogenic plasmids, FBdelPGASAF and FBdelPGASAF-fus, were transfected and the MV H and F expression constructs, pCG-H and pCG-F, were co-transfected into the panel of cell lines. Transfections were carried out using 2.5 mg of the relevant plasmids and 15 ml Superfect (Qiagen). After transfection the cells were incubated with regular medium for 48–72 hrs, until syncytia could be clearly seen, when fusion efficiency was scored (− no syncytia, + definite syncytia, ++ abundant syncytia).

Results
Cell-Cell Fusion Assays

The fusogenic and non-fusogenic plasmids and the MV H and F expression constructs were transfected into the panel of cell lines. The cells were left for 72 hours before cell-cell fusion was scored. Results of the assays are shown in Table 3. The fusogenic GALV construct shows the same pattern of fusion ability as the MV F and H proteins show.

TABLE 3

This table shows the results of cell-cell fusion assays on a panel of cell lines. − = no syncytia, + = definite syncytia, + + = abundant syncytia.

|       | FBdelPGASAF | FBdelPGASAF-fus | CG-F/CG-H |
|-------|-------------|-----------------|-----------|
| C170  | −           | ++              | ++        |
| A431  | −           | ++              | ++        |
| TE671 | −           | ++              | ++        |
| HeLa  | −           | ++              | ++        |
| NIH3T3| −           | −               | −         |

EXAMPLE 4

Display of EGF on GALV Envelope

Materials and Methods
Construction of Envelope Expression Plasmids

Envelope expression plasmid GALVMoT was constructed by PCR amplification of the cDNA encoding GaLV env from the plasmid pMOVGaLVSEATO env (Wilson et al., J. Virol. 63, 2374–2378, 1989) using primers GalvrevXba and Galvforcla2 which were tailed with XbaI and Cla 1 restriction sites. The PCR products were then ligated into the plasmid FBMoSALF after XbaI and Cla 1 digestion.

The chimeric envelope expression plasmid EXGaLVMoT was constructed by PCR amplification of the cDNA encoding GALV env from plasmid PMOVGaLVSEATO env using primers galvslq and galvforcla2. Primer "galvslq" was tailed with a Notl restriction site and contained the coding sequence for a factor Xa cleavage signal (IEGR; SEQ ID NO:14). The PCR products were ligated into the plasmid Emo after Notl and Clal digestion. The sequences of the primers are shown below. The restriction enzyme sites are underlined. The coding sequence for the factor Xa cleavage signal is shown in bold.

galvslq 5'gcaaatct<u>gcggccgca</u>atcgagggaaggagtctgcaaaataa-gaacccccaccag 3' (SEQ ID NO:5)

galvforcla2 5'cc<u>atcgatt</u>gatgcatggcccgag 3' (SEQ ID NO:6)

galvrevxba 5'ctagc<u>tctaga</u>atggtattgctgcctgggtcc 3' (SEQ ID NO:7)

The correct sequence of both constructs was confirmed by didexoysequencing. A diagrammatic representation of the constructs is shown in FIG. 7.

Vector Production

The envelope expression plasmids were transfected into the TELCeB6 complementing cell line which contains gag-pol expression plasmid and an nls LacZ retroviral vector. Stable transfectants were selected in 50 μg/ml phleomycin and pooled.

Infection of Target Cells

Supernatant from the transfected TELCeB6 complementing cell lines was harvested after the cells had been allowed to grow to confluency at 37° C. then placed at 32° C. for 1–3 days. The medium was changed and, after overnight incubation, the supernatant was harvested and filtered through a 0.45 μm filter. The filtered supernatants were then used to infect target cells. Adherent target cells were plated into six-well plates at approximately $10^5$ cells per well on the evening prior to infection and incubated overnight at 37° C. and suspension cells were plated into six well plates at approximately $10^6$cells per well one hour before infection. Filtered viral supernatant in serum free medium was added to the target cells and incubated for 2–4 hours in the presence of 8 mg/ml polybrene. For infections involving factor Xa cleavage, the virus was incubated with 4 mg/ml of factor Xa protease in the presence of 2.5 mM $CaCl_2$ for 90 mins prior to infection. The retroviral supernatant was then removed from the target cells, the medium was replaced with the usual medium and the cells were placed at 37° C. for a further 48–72 hours. X gal staining for detection of β-galactosidase activity was then carried out.

Results

Titration of GaLVMoT and EXGaLVMoT on HT1080 Cells

When these vectors were titrated on HT1080 cells, a human EGF receptor positive cell line, the titre of GaLVMoT was $10^6$ efu/ml whereas that of EXGaLVMoT was $3.6\times10^3$ efu/ml. However, when the vector supernatant was incubated with factor Xa protease prior to infection, in order to cleave the displayed domain, the titre of GaLVMoT remained at $10^6$ efu/ml whereas the titre of EXGaLVMoT was increased to $3.6\times10^4$/ml (table 4).

Titration of GaLVMoT and EXGaLVMoT on MDBK Cells

When these vectors were titrated on MDBK cells, a bovine EGF-R positive cell line, there was a similar finding. The titre of EXGaLVMoT was reduced compared to GaLVMoT but increased ten fold upon protease cleavage (table 4).

Infection of Haemopoietic Cells with EXGaLVMoT

Two EGF-R negative haemopoietic suspension cell lines, HMC-1 and Meg-O1 were infected with EXGaLVMoT and gave titres (expressed a percentage blue cells) of 28.8% and 31.65% respectively. These results are similar to those previously published with the vector EXA (Fielding et al., Blood 91, 1–10, 1998). Taken in conjunction with the above data on the EGF-R positive cells, this suggests the EXGaLV-MoT exhibits similar characteristics to the EXA vector where the displayed domain causes a reduction in infectivity in a receptor dependent manner.

TABLE 4

Titer of GaLV vectors on EGF-R positive cells

| | HT1080 | | MDBK | |
|---|---|---|---|---|
| | −Xa | +Xa | −Xa | +Xa |
| GaLVMoT | $1 \times 10^6$ | $1 \times 10^6$ | $3.5 \times 10^4$ | $2.9 \times 104$ |
| EXGaLVMoT | $3.6 \times 10^3$ | $3.6 \times 10^4$ | <1 | 12 |

Conclusions

1. Wild type (GaLVMoT) and chimeric Gibbon Ape Leukaemia virus envelope expression constructs have been constructed and incorporated into retroviral vector particles which contain MLV gag-pol core particles and a Moloney MLV nlsLacZ retroviral vector.

2. Both the wild type and EGF-chimeric vectors are capable of infecting human cell lines.

3. The titre of the EGF-chimaera is considerably reduced on EGF receptor positive cell lines and can be increased by factor Xa cleavage of the displayed domain. The largest reduction in titre is seen on cell lines with the highest density of EGF receptors.

4. Thus, display of EGF as an N terminal extension of the Gibbon Ape Leukaemia virus SU glycoprotein results in altered viral tropism which is similar to that seen with display of EGF on the murine leukaemia virus envelopes (Nilson et al., Gene Ther. 3, 280, 1996) and is likely to be EGF-receptor mediated.

Other Embodiments

Other embodiments are within the following claims.

What is claimed is:

1. A method of fusing unwanted tumor cells in a human patient, comprising administering to said patient a composition in an amount sufficient to cause fusion of said unwanted tumor cells, wherein said composition comprises a nucleic acid vector and a diluent that does not include culture serum, wherein said nucleic acid vector comprises a nucleotide sequence encoding a measles virus F glycoprotein and a nucleotide sequence encoding a measles virus H glycoprotein or a chimeric measles virus H glycoprotein comprising an EGF or IGF sequence, wherein said measles virus F glycoprotein is expressible on a eukaryotic cell surface, wherein said measles virus H glycoprotein or said chimeric measles virus H glycoprotein is expressible on a eukaryotic cell surface, and wherein said composition is directly delivered to said unwanted tumor cells.

2. A method of fusing unwanted tumor cells in a human patient, comprising administering to said patient a composition in an amount sufficient to cause fusion of said unwanted tumor cells, wherein said composition comprises a eukaryotic host cell and a diluent which does not include culture serum, wherein said eukaryotic host cell contains a nucleic acid vector comprising a nucleotide sequence encoding a measles virus F glycoprotein and a nucleotide sequence encoding a measles virus H glycoprotein or a chimeric measles virus H glycoprotein comprising an EGF or IGF sequence, wherein said measles virus F glycoprotein is expressed on the surface of said eukaryotic host cell, wherein said measles virus H glycoprotein or said chimeric measles virus H glycoprotein is expressed on the surface of said eukaryotic host cell, and wherein said composition is directly delivered to said unwanted tumor cells.

3. A method of treating a patient comprising tumor cells, said method comprising administering to said patient a therapeutically effective amount of a composition, wherein said composition comprises a nucleic acid vector and a diluent which does not include culture serum, wherein said nucleic acid vector comprises a nucleotide sequence encoding a measles virus F glycoprotein and a nucleotide sequence encoding a measles virus H glycoprotein or a chimeric measles virus H glycoprotein comprising an EGF or IGF sequence, wherein said measles virus F glycoprotein is expressible on a eukaryotic cell surface, wherein said measles virus H glycoprotein or said chimeric measles virus H glycoprotein is expressible on a eukaryotic cell surface, wherein said composition is directly delivered to said tumor cells, and wherein the number of tumor cells is reduced.

4. A method of treating a patient comprising tumor cells, said method comprising administering to said patient a therapeutically effective amount of a composition, wherein said composition comprises a eukaryotic host cell and a diluent which does not include culture serum, wherein said eukaryotic host cell contains a nucleic acid vector comprising a nucleotide sequence encoding a measles virus F glycoprotein and a nucleotide sequence encoding a measles virus H glycoprotein or a chimeric measles virus H glycoprotein comprising an EGF or IGF sequence, wherein said measles virus F glycoprotein is expressed on the surface of said eukaryotic host cell, wherein said measles virus H glycoprotein or said chimeric measles virus H glycoprotein is expressed on the surface of said eukaryotic host cell, wherein said composition is directly delivered to said tumor cells, and wherein the number of tumor cells is reduced.

* * * * *

UNITED STATES PATENT AND TRADEMARK OFFICE
CERTIFICATE OF CORRECTION

PATENT NO. : 6,750,206 B2
DATED : June 15, 2004
INVENTOR(S) : Stephen James Russell et al.

It is certified that error appears in the above-identified patent and that said Letters Patent is hereby corrected as shown below:

Title page,
Item [75], Inventors, "Francois-Loic Cosset" reference, please delete "Lyons" and insert -- Lyon -- therefor,
Item [56], References Cited, OTHER PUBLICATIONS, "Rudinger et al." reference, please delete "peptied" and insert -- peptide -- therefor; "Kaye et al." reference, please delete "singel" and insert -- single -- therefor; and "Otteken et al." reference, please delete "Truncatefd" and insert -- Truncated -- therefor;

Signed and Sealed this

Twenty-sixth Day of April, 2005

JON W. DUDAS
*Director of the United States Patent and Trademark Office*

SEQUENCE LISTING

<160> NUMBER OF SEQ ID NOS: 15

<210> SEQ ID NO 1
<211> LENGTH: 59
<212> TYPE: DNA
<213> ORGANISM: Artificial Sequence
<220> FEATURE:
<223> OTHER INFORMATION: Primer

<400> SEQUENCE: 1
ccgggaagat ggaaccaatg cggcccagcc ggcctcaggt tcagcggccg catagtaga 59

<210> SEQ ID NO 2
<211> LENGTH: 59
<212> TYPE: DNA
<213> ORGANISM: Artificial Sequence
<220> FEATURE:
<223> OTHER INFORMATION: Primer

<400> SEQUENCE: 2
ctagtctact atgcggccgc tgaacctgag gccggctggg ccgcattggt tccatcttc 59

<210> SEQ ID NO 3
<211> LENGTH: 57
<212> TYPE: DNA
<213> ORGANISM: Artificial Sequence
<220> FEATURE:
<223> OTHER INFORMATION: Primer

<400> SEQUENCE: 3
ccgggaagat ggaaccaata tcgagggaag ggcggcccag ccggcctcag gttcagc 57

<210> SEQ ID NO 4
<211> LENGTH: 57
<212> TYPE: DNA
<213> ORGANISM: Artificial Sequence
<220> FEATURE:
<223> OTHER INFORMATION: Primer

<400> SEQUENCE: 4
ggccgctgaa cctgaggccg gctgggccgc ccttccctcg atattggttc catcttc 57

<210> SEQ ID NO 5
<211> LENGTH: 56
<212> TYPE: DNA
<213> ORGANISM: Artificial Sequence
<220> FEATURE:
<223> OTHER INFORMATION: Primer

<400> SEQUENCE: 5
gcaaatctgc ggccgcaatc gagggaagga gtctgcaaaa taagaacccc caccag     56

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
ccatcgattg atgcatggcc cgag     24

<210> SEQ ID NO 7
<211> LENGTH: 32
<212> TYPE: DNA
<213> ORGANISM: Artificial Sequence
<220> FEATURE:
<223> OTHER INFORMATION: Primer

<400> SEQUENCE: 7
ctagctctag aatggtattg ctgcctgggt cc     32

<210> SEQ ID NO 8
<211> LENGTH: 24
<212> TYPE: PRT
<213> ORGANISM: Artificial Sequence
<220> FEATURE:
<223> OTHER INFORMATION: Plasmid Sequence

<400> SEQUENCE: 8

Arg Glu Asp Gly Thr Asn Ala Ala Gln Pro Ala Met Ala Asn Ser Asp
 1               5                  10                  15

Ser Trp Trp Glu Leu Ala Ala Ala
            20

<210> SEQ ID NO 9
<211> LENGTH: 28
<212> TYPE: PRT
<213> ORGANISM: Artificial Sequence
<220> FEATURE:
<223> OTHER INFORMATION: Plasmid Sequence

<400> SEQUENCE: 9

Arg Glu Asp Gly Thr Asn Ile Glu Gly Arg Ala Ala Gln Pro Ala Met
 1               5                  10                  15

Ala Asn Ser Asp Ser Trp Trp Glu Leu Ala Ala Ala
            20                  25

<210> SEQ ID NO 10
<211> LENGTH: 24
<212> TYPE: PRT
<213> ORGANISM: Artificial Sequence
<220> FEATURE:
<223> OTHER INFORMATION: Plasmid Sequence

<400> SEQUENCE: 10

Arg Glu Asp Gly Thr Asn Ala Ala Gln Pro Ala Gly Pro Glu Thr Leu

-continued

```
         1               5              10              15

Cys Ala Lys Ser Ala Ala Ala Ala
             20

<210> SEQ ID NO 11
<211> LENGTH: 28
<212> TYPE: PRT
<213> ORGANISM: Artificial Sequence
<220> FEATURE:
<223> OTHER INFORMATION: Plasmid Sequence

<400> SEQUENCE: 11

Arg Glu Asp Gly Thr Asn Ile Glu Gly Arg Ala Ala Gln Pro Ala Gly
 1               5                  10                  15

Pro Glu Thr Leu Cys Ala Lys Ser Ala Ala Ala
             20                  25

<210> SEQ ID NO 12
<211> LENGTH: 2004
<212> TYPE: DNA
<213> ORGANISM: Artificial Sequence
<220> FEATURE:
<223> OTHER INFORMATION: Plasmid sequence
<220> FEATURE:
<221> NAME/KEY: CDS
<222> LOCATION: (1)...(2001)

<400> SEQUENCE: 12 atg gta ttg ctg cct ggg tcc atg ctt ctc acc tca aac ctg cac cac      48
Met Val Leu Leu Pro Gly Ser Met Leu Leu Thr Ser Asn Leu His His
 1               5                  10                  15 ctt cgg cac cag atg agt cct ggg agc tgg aaa aga ctg atc atc ctc      96
Leu Arg His Gln Met Ser Pro Gly Ser Trp Lys Arg Leu Ile Ile Leu
             20                  25                  30 tta agc tgc gta ttc ggc ggc ggc ggg acg agt ctg caa aat aag aac     144
Leu Ser Cys Val Phe Gly Gly Gly Gly Thr Ser Leu Gln Asn Lys Asn
         35                  40                  45 ccc cac cag ccc atg acc ctc act tgg cag gta ctg tcc caa act gga     192
Pro His Gln Pro Met Thr Leu Thr Trp Gln Val Leu Ser Gln Thr Gly
     50                  55                  60 gac gtt gtc tgg gat aca aag gca gtc cag ccc cct tgg act tgg tgg     240
Asp Val Val Trp Asp Thr Lys Ala Val Gln Pro Pro Trp Thr Trp Trp
 65                  70                  75                  80 ccc aca ctt aaa cct gat gta tgt gcc ttg gcg gct agt ctt gag tcc     288
Pro Thr Leu Lys Pro Asp Val Cys Ala Leu Ala Ala Ser Leu Glu Ser
                 85                  90                  95 tgg gat atc ccg gga acc gat gtc tcg tcc tct aaa cga gtc aga cct     336
Trp Asp Ile Pro Gly Thr Asp Val Ser Ser Ser Lys Arg Val Arg Pro
            100                 105                 110 ccg gac tca gac tat act gcc gct tat aag caa atc acc tgg gga gcc     384
Pro Asp Ser Asp Tyr Thr Ala Ala Tyr Lys Gln Ile Thr Trp Gly Ala
        115                 120                 125 ata ggg tgc agc tac cct cgg gct agg act aga atg gca agc tct acc     432
Ile Gly Cys Ser Tyr Pro Arg Ala Arg Thr Arg Met Ala Ser Ser Thr
    130                 135                 140 ttc tac gta tgt ccc cgg gat ggc cgg acc ctt tca gaa gct aga agg     480
Phe Tyr Val Cys Pro Arg Asp Gly Arg Thr Leu Ser Glu Ala Arg Arg
145                 150                 155                 160 tgc ggg ggg cta gaa tcc cta tac tgt aaa gaa tgg gat tgt gag acc     528
Cys Gly Gly Leu Glu Ser Leu Tyr Cys Lys Glu Trp Asp Cys Glu Thr
                165                 170                 175 acg ggg acc ggt tat tgg cta tct aaa tcc tca aaa gac ctc ata act     576
```

```
                  Thr Gly Thr Gly Tyr Trp Leu Ser Lys Ser Ser Lys Asp Leu Ile Thr
                                  180                 185                 190 gta aaa tgg gac caa aat agc gaa tgg act caa aaa ttt caa cag tgt          624
Val Lys Trp Asp Gln Asn Ser Glu Trp Thr Gln Lys Phe Gln Gln Cys
            195                 200                 205 cac cag acc ggc tgg tgt aac ccc ctt aaa ata gat ttc aca gac aaa          672
His Gln Thr Gly Trp Cys Asn Pro Leu Lys Ile Asp Phe Thr Asp Lys
210                 215                 220 gga aaa tta tcc aag gac tgg ata acg gga aaa acc tgg gga tta aga          720
Gly Lys Leu Ser Lys Asp Trp Ile Thr Gly Lys Thr Trp Gly Leu Arg
225                 230                 235                 240 ttc tat gtg tct gga cat cca ggc gta cag ttc acc att cgc tta aaa          768
Phe Tyr Val Ser Gly His Pro Gly Val Gln Phe Thr Ile Arg Leu Lys
                245                 250                 255 atc acc aac atg cca gct gtg gca gta ggt cct gac ctc gtc ctt gtg          816
Ile Thr Asn Met Pro Ala Val Ala Val Gly Pro Asp Leu Val Leu Val
            260                 265                 270 gaa caa gga cct cct aga acg tcc ctc gct ctc cca cct cct ctt ccc          864
Glu Gln Gly Pro Pro Arg Thr Ser Leu Ala Leu Pro Pro Pro Leu Pro
        275                 280                 285 cca agg gaa gcg cca ccg cca tct ctc ccc gac tct aac tcc aca gcc          912
Pro Arg Glu Ala Pro Pro Pro Ser Leu Pro Asp Ser Asn Ser Thr Ala
    290                 295                 300 ctg gcg act agt gca caa act ccc acg gtg aga aaa aca att gtt acc          960
Leu Ala Thr Ser Ala Gln Thr Pro Thr Val Arg Lys Thr Ile Val Thr
305                 310                 315                 320 cta aac act ccg cct ccc acc aca ggc gac aga ctt ttt gat ctt gtg         1008
Leu Asn Thr Pro Pro Pro Thr Thr Gly Asp Arg Leu Phe Asp Leu Val
                325                 330                 335 cag ggg gcc ttc cta acc tta aat gct acc aac cca ggg gcc act gag         1056
Gln Gly Ala Phe Leu Thr Leu Asn Ala Thr Asn Pro Gly Ala Thr Glu
            340                 345                 350 tct tgc tgg ctt tgt ttg gcc atg ggc ccc cct tat tat gaa gca ata         1104
Ser Cys Trp Leu Cys Leu Ala Met Gly Pro Pro Tyr Tyr Glu Ala Ile
        355                 360                 365 gcc tca tca gga gag gtc gcc tac tcc acc gac ctt gac cgg tgc cgc         1152
Ala Ser Ser Gly Glu Val Ala Tyr Ser Thr Asp Leu Asp Arg Cys Arg
    370                 375                 380 tgg ggg acc caa gga aag ctc acc ctc act gag gtc tca gga cac ggg         1200
Trp Gly Thr Gln Gly Lys Leu Thr Leu Thr Glu Val Ser Gly His Gly
385                 390                 395                 400 ttg tgc ata gga aag gtg ccc ttt acc cat cag cat ctc tgc aat cag         1248
Leu Cys Ile Gly Lys Val Pro Phe Thr His Gln His Leu Cys Asn Gln
                405                 410                 415 acc cta tcc atc aat tcc tcc gga gac cat cag tat ctg ctc ccc tcc         1296
Thr Leu Ser Ile Asn Ser Ser Gly Asp His Gln Tyr Leu Leu Pro Ser
            420                 425                 430 aac cat agc tgg tgg gct tgc agc act ggc ctc acc cct tgc ctc tcc         1344
Asn His Ser Trp Trp Ala Cys Ser Thr Gly Leu Thr Pro Cys Leu Ser
        435                 440                 445 acc tca gtt ttt aat cag act aga gat ttc tgt atc cag gtc cag ctg         1392
Thr Ser Val Phe Asn Gln Thr Arg Asp Phe Cys Ile Gln Val Gln Leu
    450                 455                 460 att cct cgc atc tat tac tat cct gaa gaa gtt ttg tta cag gcc tat         1440
Ile Pro Arg Ile Tyr Tyr Tyr Pro Glu Glu Val Leu Leu Gln Ala Tyr
465                 470                 475                 480 gac aat tct cac ccc agg act aaa aga gag gct gtc tca ctt acc cta         1488
Asp Asn Ser His Pro Arg Thr Lys Arg Glu Ala Val Ser Leu Thr Leu
                485                 490                 495
```

-continued

```
gct gtt tta ctg ggg ttg gga atc acg gcg gga ata ggt act ggt tca    1536
Ala Val Leu Leu Gly Leu Gly Ile Thr Ala Gly Ile Gly Thr Gly Ser
            500                 505                 510 act gcc tta att aaa gga cct ata gac ctc cag caa ggc ctg aca agc    1584
Thr Ala Leu Ile Lys Gly Pro Ile Asp Leu Gln Gln Gly Leu Thr Ser
            515                 520                 525 ctc cag atc gcc ata gat gct gac ctc cgg gcc ctc caa gac tca gtc    1632
Leu Gln Ile Ala Ile Asp Ala Asp Leu Arg Ala Leu Gln Asp Ser Val
        530                 535                 540 agc aag tta gag gac tca ctg act tcc ctg tcc gag gta gtg ctc caa    1680
Ser Lys Leu Glu Asp Ser Leu Thr Ser Leu Ser Glu Val Val Leu Gln
545                 550                 555                 560 aat agg aga ggc ctt gac ttg ctg ttt cta aaa gaa ggt ggc ctc tgt    1728
Asn Arg Arg Gly Leu Asp Leu Leu Phe Leu Lys Glu Gly Gly Leu Cys
                565                 570                 575 gcg gcc cta aag gaa gag tgc tgt ttt tac ata gac cac tca ggt gca    1776
Ala Ala Leu Lys Glu Glu Cys Cys Phe Tyr Ile Asp His Ser Gly Ala
            580                 585                 590 gta cgg gac tcc atg aaa aaa ctc aaa gaa aaa ctg gat aaa aga cag    1824
Val Arg Asp Ser Met Lys Lys Leu Lys Glu Lys Leu Asp Lys Arg Gln
        595                 600                 605 tta gag cgc cag aaa agc caa aac tgg tat gaa gga tgg ttc aat aac    1872
Leu Glu Arg Gln Lys Ser Gln Asn Trp Tyr Glu Gly Trp Phe Asn Asn
610                 615                 620 tcc cct tgg ttc act acc ctg cta tca acc atc gct ggg ccc cta tta    1920
Ser Pro Trp Phe Thr Thr Leu Leu Ser Thr Ile Ala Gly Pro Leu Leu
625                 630                 635                 640 ctc ctc ctt ctg ttg ctc atc ctc ggg cca tgc atc atc aat aag tta    1968
Leu Leu Leu Leu Leu Leu Ile Leu Gly Pro Cys Ile Ile Asn Lys Leu
                645                 650                 655 gtt caa ttc atc aat gat agg ata agt gca tgt taa                    2004
Val Gln Phe Ile Asn Asp Arg Ile Ser Ala Cys
            660                 665
```

<210> SEQ ID NO 13
<211> LENGTH: 667
<212> TYPE: PRT
<213> ORGANISM: Artificial Sequence
<220> FEATURE:
<223> OTHER INFORMATION: Plasmid sequence

<400> SEQUENCE: 13

```
Met Val Leu Leu Pro Gly Ser Met Leu Leu Thr Ser Asn Leu His His
1               5                   10                  15

Leu Arg His Gln Met Ser Pro Gly Ser Trp Lys Arg Leu Ile Ile Leu
            20                  25                  30

Leu Ser Cys Val Phe Gly Gly Gly Thr Ser Leu Gln Asn Lys Asn
        35                  40                  45

Pro His Gln Pro Met Thr Leu Thr Trp Gln Val Leu Ser Gln Thr Gly
    50                  55                  60

Asp Val Val Trp Asp Thr Lys Ala Val Gln Pro Pro Trp Thr Trp Trp
65                  70                  75                  80

Pro Thr Leu Lys Pro Asp Val Cys Ala Leu Ala Ala Ser Leu Glu Ser
                85                  90                  95

Trp Asp Ile Pro Gly Thr Asp Val Ser Ser Lys Arg Val Arg Pro
            100                 105                 110

Pro Asp Ser Asp Tyr Thr Ala Ala Tyr Lys Gln Ile Thr Trp Gly Ala
        115                 120                 125

Ile Gly Cys Ser Tyr Pro Arg Ala Arg Thr Arg Met Ala Ser Ser Thr
```

```
                130              135              140
    Phe Tyr Val Cys Pro Arg Asp Gly Arg Thr Leu Ser Glu Ala Arg Arg
    145              150              155              160
    Cys Gly Gly Leu Glu Ser Leu Tyr Cys Lys Glu Trp Asp Cys Glu Thr
                    165              170              175
    Thr Gly Thr Gly Tyr Trp Leu Ser Lys Ser Ser Lys Asp Leu Ile Thr
                180              185              190
    Val Lys Trp Asp Gln Asn Ser Glu Trp Thr Gln Lys Phe Gln Gln Cys
                195              200              205
    His Gln Thr Gly Trp Cys Asn Pro Leu Lys Ile Asp Phe Thr Asp Lys
                210              215              220
    Gly Lys Leu Ser Lys Asp Trp Ile Thr Gly Lys Thr Trp Gly Leu Arg
    225              230              235              240
    Phe Tyr Val Ser Gly His Pro Gly Val Gln Phe Thr Ile Arg Leu Lys
                    245              250              255
    Ile Thr Asn Met Pro Ala Val Ala Val Gly Pro Asp Leu Val Leu Val
                    260              265              270
    Glu Gln Gly Pro Pro Arg Thr Ser Leu Ala Leu Pro Pro Pro Leu Pro
                275              280              285
    Pro Arg Glu Ala Pro Pro Ser Leu Pro Asp Ser Asn Ser Thr Ala
                290              295              300
    Leu Ala Thr Ser Ala Gln Thr Pro Thr Val Arg Lys Thr Ile Val Thr
    305              310              315              320
    Leu Asn Thr Pro Pro Thr Thr Gly Asp Arg Leu Phe Asp Leu Val
                    325              330              335
    Gln Gly Ala Phe Leu Thr Leu Asn Ala Thr Asn Pro Gly Ala Thr Glu
                    340              345              350
    Ser Cys Trp Leu Cys Leu Ala Met Gly Pro Pro Tyr Tyr Glu Ala Ile
                    355              360              365
    Ala Ser Ser Gly Glu Val Ala Tyr Ser Thr Asp Leu Asp Arg Cys Arg
    370              375              380
    Trp Gly Thr Gln Gly Lys Leu Thr Leu Thr Glu Val Ser Gly His Gly
    385              390              395              400
    Leu Cys Ile Gly Lys Val Pro Phe Thr His Gln His Leu Cys Asn Gln
                    405              410              415
    Thr Leu Ser Ile Asn Ser Ser Gly Asp His Gln Tyr Leu Leu Pro Ser
                    420              425              430
    Asn His Ser Trp Trp Ala Cys Ser Thr Gly Leu Thr Pro Cys Leu Ser
                    435              440              445
    Thr Ser Val Phe Asn Gln Thr Arg Asp Phe Cys Ile Gln Val Gln Leu
                450              455              460
    Ile Pro Arg Ile Tyr Tyr Tyr Pro Glu Glu Val Leu Leu Gln Ala Tyr
    465              470              475              480
    Asp Asn Ser His Pro Arg Thr Lys Arg Glu Ala Val Ser Leu Thr Leu
                    485              490              495
    Ala Val Leu Leu Gly Leu Gly Ile Thr Ala Gly Ile Gly Thr Gly Ser
                    500              505              510
    Thr Ala Leu Ile Lys Gly Pro Ile Asp Leu Gln Gln Gly Leu Thr Ser
                    515              520              525
    Leu Gln Ile Ala Ile Asp Ala Asp Leu Arg Ala Leu Gln Asp Ser Val
                530              535              540
    Ser Lys Leu Glu Asp Ser Leu Thr Ser Leu Ser Glu Val Val Leu Gln
    545              550              555              560
```

```
Asn Arg Arg Gly Leu Asp Leu Leu Phe Leu Lys Glu Gly Gly Leu Cys
            565                 570                 575

Ala Ala Leu Lys Glu Glu Cys Cys Phe Tyr Ile Asp His Ser Gly Ala
            580                 585                 590

Val Arg Asp Ser Met Lys Lys Leu Lys Glu Lys Leu Asp Lys Arg Gln
            595                 600                 605

Leu Glu Arg Gln Lys Ser Gln Asn Trp Tyr Glu Gly Trp Phe Asn Asn
        610                 615                 620

Ser Pro Trp Phe Thr Thr Leu Leu Ser Thr Ile Ala Gly Pro Leu Leu
625                 630                 635                 640

Leu Leu Leu Leu Leu Leu Ile Leu Gly Pro Cys Ile Ile Asn Lys Leu
                645                 650                 655

Val Gln Phe Ile Asn Asp Arg Ile Ser Ala Cys
            660                 665

<210> SEQ ID NO 14
<211> LENGTH: 4
<212> TYPE: PRT
<213> ORGANISM: Artificial Sequence
<220> FEATURE:
<223> OTHER INFORMATION: Cleavage Signal

<400> SEQUENCE: 14

Ile Glu Gly Arg
 1

<210> SEQ ID NO 15
<211> LENGTH: 6
<212> TYPE: PRT
<213> ORGANISM: Artificial Sequence
<220> FEATURE:
<223> OTHER INFORMATION: Cleavage Site

<400> SEQUENCE: 15

Pro Leu Gly Leu Trp Ala
 1               5
```